US007666397B2

(12) United States Patent
Huang et al.

(10) Patent No.: US 7,666,397 B2
(45) Date of Patent: *Feb. 23, 2010

(54) PEPTIDE-BASED CONDITIONERS AND COLORANTS FOR HAIR, SKIN, AND NAILS

(75) Inventors: Xueying Huang, Hockessin, DE (US); Hong Wang, Kennett Square, PA (US); Ying Wu, Wallingford, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 35 days.

This patent is subject to a terminal disclaimer.

(21) Appl. No.: 11/592,108

(22) Filed: Nov. 2, 2006

(65) Prior Publication Data

US 2007/0053857 A1  Mar. 8, 2007

Related U.S. Application Data

(62) Division of application No. 10/935,642, filed on Sep. 7, 2004, now Pat. No. 7,220,405.

(60) Provisional application No. 60/501,498, filed on Sep. 8, 2003, provisional application No. 60/562,645, filed on Apr. 15, 2004.

(51) Int. Cl.
A61K 8/64 (2006.01)
C07K 7/06 (2006.01)
C07K 7/08 (2006.01)

(52) U.S. Cl. ............ 424/63; 424/64; 424/78.03; 530/327; 530/329; 530/345

(58) Field of Classification Search .......... None
See application file for complete search history.

(56) References Cited

U.S. PATENT DOCUMENTS

| | | | |
|---|---|---|---|
| 4,416,873 A | 11/1983 | Puchalski et al. | |
| 4,482,537 A | 11/1984 | El-Menshawy et al. | |
| 5,192,332 A | 3/1993 | Lang et al. | |
| 5,223,409 A | 6/1993 | Ladner et al. | |
| 5,403,484 A | 4/1995 | Ladner et al. | |
| 5,425,937 A | 6/1995 | Uchiwa et al. | |
| 5,449,754 A | 9/1995 | Nishioka | |
| 5,480,971 A | 1/1996 | Houghten et al. | |
| 5,490,980 A | 2/1996 | Richardson et al. | |
| 5,571,698 A | 11/1996 | Ladner et al. | |
| 5,585,275 A | 12/1996 | Hudson et al. | |
| 5,597,386 A | 1/1997 | Igarashi et al. | |
| 5,639,603 A | 6/1997 | Dower et al. | |
| 5,801,226 A | 9/1998 | Cummins et al. | |
| 5,814,343 A * | 9/1998 | Jones et al. ............ 424/499 |
| 5,837,500 A | 11/1998 | Ladner et al. | |
| 6,013,250 A | 1/2000 | Cannell et al. | |
| 6,190,681 B1 * | 2/2001 | Fishman ............ 424/401 |
| 6,232,287 B1 | 5/2001 | Ruoslahti et al. | |
| 6,267,957 B1 | 7/2001 | Green et al. | |
| 6,280,747 B1 | 8/2001 | Philippe et al. | |
| 6,344,443 B1 | 2/2002 | Liu et al. | |
| 6,537,330 B1 | 3/2003 | Hoeffkes et al. | |
| 6,620,419 B1 | 9/2003 | Lintner | |
| 7,309,482 B2 * | 12/2007 | Buseman-Williams et al. ... 424/59 |
| 2002/0098524 A1 | 7/2002 | Murray et al. | |
| 2003/0152976 A1 | 8/2003 | Janssen et al. | |
| 2003/0185870 A1 | 10/2003 | Grinstaff et al. | |

FOREIGN PATENT DOCUMENTS

| | | |
|---|---|---|
| CA | 2563999 A1 | 12/2005 |
| EP | 0 453 097 A2 | 10/1991 |
| EP | 0570583 A1 | 11/1993 |
| EP | 0634161 A1 | 1/1995 |
| EP | 0736544 B1 | 10/1996 |
| JP | 02311412 A | 12/1990 |
| JP | 06065049 A | 3/1994 |
| JP | 08104614 A | 4/1996 |
| JP | 09003100 A | 1/1997 |
| JP | 2002363026 | 12/2002 |
| WO | WO 00/48558 | 8/2000 |
| WO | WO 01/07009 A1 | 2/2001 |
| WO | WO 01/45652 A1 | 6/2001 |

(Continued)

OTHER PUBLICATIONS

S. G. Dixit et al., Combinatorial Chemistry—Principles and Practices, Journal of Scientific & Industrial Research, vol. 57:173-183, 1998.

(Continued)

*Primary Examiner*—Jeffrey E Russel

(57) ABSTRACT

Peptides have been identified that bind with high affinity to hair, skin, and nails. Peptide-based hair conditioners, hair colorants, skin conditioners, skin colorants, and nail colorants are described. The peptide-based hair conditioners and hair colorants consist of a hair-binding peptide coupled to a hair conditioning agent or a coloring agent, respectively. The peptide-based skin conditioners and skin colorants consist of a skin-binding peptide coupled to a skin conditioning agent or a colorant, respectively. The peptide-based nail colorants consist of a nail-binding peptide coupled to a coloring agent. In all these compositions, the peptide may be directly coupled to the active agent or the coupling may be via a spacer. Personal care compositions containing these peptide-based conditioners and colorants are also described.

16 Claims, No Drawings

FOREIGN PATENT DOCUMENTS

| | | |
|---|---|---|
| WO | WO 01/79479 A2 | 10/2001 |
| WO | WO 02/065134 A2 | 8/2002 |
| WO | WO 03/031477 A1 | 4/2003 |
| WO | WO 03/102020 A2 | 12/2003 |
| WO | WO 04/000257 A2 | 12/2003 |
| WO | WO 2004/048399 A2 | 6/2004 |
| WO | WO 2004/069211 A2 | 8/2004 |
| WO | 2005117537 A | 12/2005 |
| WO | WO 2005/115306 A2 | 12/2005 |
| WO | WO 2006/097432 A2 | 9/2006 |
| WO | WO 2006/136607 A2 | 12/2006 |
| WO | WO 2007/060116 A2 | 5/2007 |
| WO | WO 2007/060117 A2 | 5/2007 |
| WO | WO 2007/063024 A2 | 6/2007 |

OTHER PUBLICATIONS

Ronald H. Hoess, Protein Design and Phage Display, Chem. Rev., vol. 101:3205-3218, 2001.

Todd C. Holmes, Novel peptide-based biomaterial scaffolds for tissue engineering, Trends in Biotechnology, vol. 20(1):16-21, 2002.

Sandra R. Whaley et al., Selection of peptides with semiconductor binding specificity for directed nanocrystal assembly, Nature, vol. 405:665-668, 2000.

Marc S. Reisch, Ingredients makers take lessons from biotechnology to mastermind the latest in personal care, C&EN Northeast News Bureau, pp. 16-21, 2002.

David J. Kemp et al., Direct immunoassay for detecting *Escherichia coli* colonies that contain polypeptides encoded by cloned DNA segments, PNAS, vol. 78(7):4520-4524, 1981.

Cheng-Ting Chien et al., The two-hybrid system: A method to identify and clone genes for proteins that interact with a protein of interest, PNAS, vol. 88:9578-9582, 1991.

David M. Helfman et al., Identification of clones that encode chicken tropomyosin by direct immunological screening of a cDNA expression library, PNAS, vol. 80:31-35, 1983.

Maria Dani, Biological Libraries, J. of Receptor & Signal Transduction Research, vol. 21(4):447-468, 2001.

Genencor International, Bio Conference, San Francisco, California, Jun. 8, 2004—Meeting Presentation, pp. 1-29.

Supplementary European Search Report Dated Aug. 11, 2008, EP Application No. 04788667.

* cited by examiner

PEPTIDE-BASED CONDITIONERS AND COLORANTS FOR HAIR, SKIN, AND NAILS

CROSS REFERENCE TO RELATED APPLICATIONS

This patent application is a divisional of U.S. patent application Ser. No. 10/935,642, filed Sep. 7, 2004, now granted as U.S. Pat. No. 7,220,405, which claims benefit of both U.S. Provisional Patent Application, 60/501,498, filed Sep. 8, 2003 and U.S. Provisional Patent Application, 60/562,645, filed Apr. 15, 2004, now expired.

The invention relates to the field of personal care products. More specifically, the invention relates to skin conditioners, hair conditioners, hair colorants, nail colorants, and skin colorants based upon specific skin-binding, hair-binding, and nail-binding peptides.

BACKGROUND OF THE INVENTION

Film-forming substances are widely used in compositions for skin and hair care as conditioning agents and moisturizers, and to protect the skin and hair against environmental and chemical damage. These substances adsorb onto and/or absorb into the skin or hair, forming a protective coating. Commonly used film-forming substances include synthetic polymers, such as silicones, polyvinylpyrrolidone, acrylic acid polymers, and polysaccharides, and proteins, such as collagen, keratin, elastin, casein, silk, and soy proteins. Many proteins are known to be particularly effective film-forming agents. Because of their low solubility at the conditions used in skin and hair care products, proteins are commonly used in the form of peptides, formed by the hydrolysis of the proteins.

In hair care and hair coloring compositions, film-forming substances are used to form a protective film on the surface of the hair to protect it from damage due to grooming and styling, shampooing, and exposure to ultraviolet light and the reactive chemicals commonly used in permanent wave agents, hair coloring products, bleaches, and hair straighteners, which denature the hair keratin protein. Moreover, these film-forming substances improve the elasticity of the hair. Film-forming substances that have been used in hair care products include proteins, such as keratin, collagen, soy, and silk proteins and hydrolysates thereof, and polymeric materials, such as polyacrylates, long chain alkyl quaternized amines, and siloxane polymers. For example, Cannell at al. in U.S. Pat. No. 6,013,250 describe a hair care composition for treating hair against chemical and ultraviolet light damage. That composition comprises hydrolyzed protein, having an abundance of anionic amino acids, particularly, sulfur-containing amino acids, and divalent cations. It is proposed in that disclosure that the anionic components of the hydrolyzed protein bind to the hair by means of cationic bridges. Amino acids and their derivatives have also been used in hair care compositions to condition and strengthen hair. For example, O'Toole et al. in WO 0051556 describe hair care compositions containing four or more amino acid compounds selected from histidine, lysine, methionine, tyrosine, tryptophan, and cysteine compounds.

Film-forming substances are also used in skin care compositions to form a protective film on the skin. These films can serve to lubricate and coat the skin to passively impede the evaporation of moisture and smooth and soften the skin. Commonly used film-forming substances in skin care compositions include hydrolyzed animal and vegetable proteins (Puchalski et al., U.S. Pat. No. 4,416,873, El-Menshawy et al., U.S. Pat. No. 4,482,537, and Kojima et al., JP 02311412) and silk proteins (Philippe et al., U.S. Pat. No. 6,280,747 and Fahnestock et al., copending U.S. patent application Ser. No. 10/704,337). Amino acids and derivatives have also been used in skin care compositions as conditioning agents. For example, Kojima et al. in JP 06065049 describe skin care compositions containing amino acids and/or their derivatives and docosahexaenoic acid, its salts or its esters.

Hair coloring agents may be divided into three categories, specifically, permanent, semi-permanent or direct, and temporary. The permanent hair dyes are generally oxidative dyes that provide hair color that lasts about four to six weeks. These oxidative hair dyes consist of two parts, one part contains the oxidative dyes in addition to other ingredients, while the second part contains an oxidizing agent such as hydrogen peroxide. The two components are mixed immediately prior to use. The oxidizing agent oxidizes the dye precursors, which then combine to form large color molecules within the hair shaft. Although the oxidative hair dyes provide long-lasting color, the oxidizing agents they contain cause hair damage. The semi-permanent or direct hair dyes are preformed dye molecules that are applied to the hair and provide color for about six to twelve shampoos. This type of hair dye is gentler to the hair because it does not contain peroxides, but the hair color does not last as long. Some improved durability is achieved by the use of nanoparticle hair coloring materials with a particle size of 10 to 500 nm, as described by Hensen et al. in WO 01045652. These nanoparticle hair coloring materials are conventional direct hair dyes that are treated to obtain nanoscale dimensions and exhibit increased absorption into the hair. Temporary hair dyes are coloring agents that are applied to the hair surface and are removed after one shampoo. It would be desirable to develop a hair coloring agent that provides the durability of the permanent hair dyes without the use of oxidizing agents that damage hair.

The major problem with the current skin care and hair care compositions, non-oxidative hair dyes, as well as nail coloring agents is that they lack the required durability required for long-lasting effects. For this reason, there have been attempts to enhance the binding of the cosmetic agent to the hair, skin or nails. For example, Richardson et al. in U.S. Pat. No. 5,490,980 and Green et al. in U.S. Pat. No. 6,267,957 describe the covalent attachment of cosmetic agents, such as skin conditioners, hair conditioners, coloring agents, sunscreens, and perfumes, to hair, skin, and nails using the enzyme transglutaminase. This enzyme crosslinks an amine moiety in the cosmetic agent to the glutamine residues in skin, hair, and nails. Similarly, Green et al. in WO 0107009 describe the use of the enzyme lysine oxidase to covalently attach cosmetic agents to hair, skin, and nails.

In another approach, cosmetic agents have been covalently attached to proteins or protein hydrolyzates. For example, Lang et al. in U.S. Pat. No. 5,192,332 describe temporary coloring compositions that contain an animal or vegetable protein, or hydrolysate thereof, which contain residues of dye molecules grafted onto the protein chain. In those compositions, the protein serves as a conditioning agent and does not enhance the binding of the cosmetic agent to hair, skin, or nails. Horikoshi et al. in JP 08104614 and Igarashi et al. in U.S. Pat. No. 5,597,386 describe hair coloring agents that consist of an anti-keratin antibody covalently attached to a dye or pigment. The antibody binds to the hair, thereby enhancing the binding of the hair coloring agent to the hair. Similarly, Kizawa et al. in JP 09003100 describe an antibody that recognizes the surface layer of hair and its use to treat hair. A hair coloring agent consisting of that anti-hair antibody coupled to colored latex particles is also described. The use of antibodies to enhance the binding of dyes to the hair is effective in increasing the durability of the hair coloring, but these antibodies are difficult and expensive to produce. Terada et al. in JP 2002363026 describe the use of conjugates consisting of single-chain antibodies, preferably anti-keratin, coupled to dyes, ligands, and cosmetic agents for skin and hair care compositions. The single-chain antibodies may be prepared using genetic engineering techniques, but are still difficult and expensive to prepare because of their large size. Findlay in WO 00048558 describes the use of calycin proteins, such as β-lactoglobulin, which contain a binding domain for a cosmetic agent and another binding domain that binds to at least a part of the surface of a hair fiber or skin surface, for conditioners, dyes, and perfumes. Again these proteins are large and difficult and expensive to produce.

Linter in U.S. Pat. No. 6,620,419 describes peptides grafted to a fatty acid chain and their use in cosmetic and dermopharmaceutical applications. The peptides described in that disclosure are chosen because they stimulate the synthesis of collagen; they are not specific binding peptides that enhance the durability of hair and skin conditioners, and hair, nail, and skin colorants.

Since its introduction in 1985, phage display has been widely used to discover a variety of ligands including peptides, proteins and small molecules for drug targets (Dixit, *J. of Sci. & Ind. Research*, 57:173-183 (1998)). The applications have expanded to other areas such as studying protein folding, novel catalytic activities, DNA-binding proteins with novel specificities, and novel peptide-based biomaterial scaffolds for tissue engineering (Hoess, *Chem. Rev.* 101:3205-3218 (2001) and Holmes, *Trends Biotechnol.* 20:16-21 (2002)). Whaley et al. (*Nature* 405:665-668 (2000)) disclose the use of phage display screening to identify peptide sequences that can bind specifically to different crystallographic forms of inorganic semiconductor substrates.

A modified screening method that comprises contacting a peptide library with an anti-target to remove peptides that bind to the anti-target, then contacting the non-binding peptides with the target has been described (Estell et al. WO 0179479, Murray et al. U.S. Patent Application Publication No. 2002/0098524, and Janssen et al. U.S. Patent Application Publication No. 2003/0152976). Using that method, a peptide sequence that binds to hair and not to skin, given as SEQ ID NO:1, and a peptide sequence that binds to skin and not hair, given as SEQ ID NO:2, were identified. Using the same method, Janssen et al. (WO 04048399) identified other skin-binding and hair-binding peptides, as well as several binding motifs. Although the potential use of these peptides in personal care applications is suggested in those disclosures, the covalent coupling of these peptides to coloring agents and conditioning agents to prepare high-affinity hair conditioners, skin conditioners, hair colorants, nail colorants and skin colorants is not described. A method for identifying high-affinity phage-peptide clones is also described in those disclosures. The method involves using PCR to identify peptides that remain bound to the target after acid elution.

Reisch (*Chem. Eng. News* 80:16-21 (2002)) reports that a family of peptides designed to target an ingredient of specific human tissue has been developed for personal care applications. However, no description of peptide-based conditioners or coloring agents are disclosed in that publication.

One of the peptide binding sequences of the instant invention, given as SEQ ID NO:3, has been reported for several other purposes. For example, Hupp et al. in WO 02065134 disclose the peptide sequence SEQ ID NO:3 as a peptide for use in modulating the binding of a p53 polypeptide to a p300 polypeptide, useful for regulating the mammalian cell cycle or to induce or prevent cell death. Liu et al. in U.S. Pat. No. 6,344,443 describe the use of that same peptide sequence to inhibit binding of tumor necrosis factor alpha to its receptor for preventing or reversing inflammatory changes in patients with arthritis and other inflammatory diseases. Another peptide binding sequence of the instant invention, given as SEQ ID NO:4, was reported by Jagota et al. in WO 03102020 as a carbon nanotube-binding peptide.

In view of the above, a need exists for hair and skin conditioners, and hair nail, and skin colorants that provide improved durability for long lasting effects and are easy and inexpensive to prepare.

Applicants have met the stated needs by identifying peptide sequences using phage display screening that specifically bind to hair, skin, and nails with high affinity and using them to design peptide-based hair conditioners, skin conditioners, hair colorants, nail colorants, and skin colorants.

SUMMARY OF THE INVENTION

The invention provides peptide sequences that bind with high affinity to hair, skin and nails. The invention also provides peptide-based conditioners and colorants for hair, skin, and nails. In one embodiment, the peptide-based conditioners and colorants are diblock compositions.

Accordingly the invention provides a hair-binding peptide selected from the group consisting of SEQ ID NOs:5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 64, 66, 69, and 70.

Similarly the invention provides a nail-binding peptide as set forth in SEQ ID NO:60.

In another embodiment the invention provides a skin-binding peptide as set forth in SEQ ID NO:61.

In a preferred embodiment the invention provides a diblock, peptide-based hair conditioner having the general structure $(HBP)_n$-HCA, wherein a) HBP is a hair-binding peptide;
b) HCA is a hair conditioning agent; and
c) n ranges from 1 to about 1000.

Similarly the invention provides a diblock, peptide-based skin conditioner having the general structure $(SBP)_n$-SCA, wherein a) SBP is a skin-binding peptide;
b) SCA is a skin conditioning agent; and
c) n ranges from 1 to about 1000.

In an alternate embodiment the invention provides a diblock, peptide-based hair colorant having the general structure $(HBP)_n$-C, wherein a) HBP is a hair-binding peptide;
b) C is a coloring agent; and
c) n ranges from 1 to about 10,000.

In another embodiment the invention provides a diblock, peptide-based nail colorant having the general structure $(NBP)_N$-C, wherein a) NBP is a nail-binding peptide;
b) C is a coloring agent; and
c) n ranges from 1 to about 10,000.

In another embodiment the invention provides a diblock, peptide-based skin colorant having the general structure $(SBP)_N$-C, wherein a) SBP is a skin-binding peptide;
b) C is a coloring agent; and
c) n ranges from 1 to about 10,000.

In a similar embodiment the invention provides a triblock, peptide-based hair conditioner having the general structure $[(HBP)_m$-$S]_n$-HCA, wherein a) HBP is a hair-binding peptide;
b) HCA is a hair conditioning agent;
c) S is a spacer;
d) m ranges from 1 to about 50; and
e) n ranges from 1 to about 1000.

Alternatively the invention provides a triblock, peptide-based skin conditioner having the general structure $[(SBP)_m\text{-}S]_n\text{-}SCA$, wherein
a) SBP is a hair-binding peptide;
b) SCA is a skin conditioning agent;
c) S is a spacer;
d) m ranges from 1 to about 50; and
e) n ranges from 1 to about 1000.

Similarly the invention provides a triblock, peptide-based hair colorant having the general structure $[(HBP)_m\text{-}S]_n\text{-}C$, wherein
a) HBP is a hair-binding peptide;
b) C is a coloring agent;
c) S is a spacer;
d) m ranges from 1 to about 50; and
e) n ranges from 1 to about 10,000.

In another embodiment the invention provides a triblock, peptide-based nail colorant having the general structure $[(NBP)_m\text{-}S]_n\text{-}C$, wherein
a) NBP is a hair-binding peptide;
b) C is a coloring agent;
c) S is a spacer;
d) m ranges from 1 to about 50; and
e) n ranges from 1 to about 10,000.

In another embodiment the invention provides a triblock, peptide-based skin colorant having the general structure $[(SBP)_m\text{-}S]_n\text{-}C$, wherein
a) SBP is a hair-binding peptide;
b) C is a coloring agent;
c) S is a spacer;
d) m ranges from 1 to about 50; and
e) n ranges from 1 to about 10,000.

Additionally the invention provides method for generating a high affinity hair, skin, or nail-binding peptide comprising the steps of:
a) providing a library of combinatorial generated phage-peptides;
b) contacting the library of (a) with a hair, skin, or nail sample to form a reaction solution comprising:
    (i) phage-peptide-hair, phage-peptide-skin, or phage-peptide-nail complexes;
    (ii) unbound hair, skin or nail, and (iii) uncomplexed peptides;
c) isolating the phage-peptide-hair, phage-peptide-skin, or phage-peptide-nail complexes of (b);
d) eluting the weakly-bound phage-peptides from the phage-peptide complex of (b);
e) infecting bacterial host cells directly with the phage-peptide-hair, phage-peptide-skin, or phage-peptide-nail complexes remaining after step (d);
f) growing the infected cells of step (e) in a suitable growth medium; and
g) isolating and identifying the phage-peptides from the grown cells of step (f), wherein the phage-peptides have a high binding affinity for hair, skin, or nails.

In a preferred embodiment the invention provides methods for forming a protective layer of a peptide-based conditioner on hair comprising applying the composition of the invention to the hair and allowing the formation of said protective layer.

Similarly the invention provides methods for forming a protective layer of a peptide-based conditioner on skin or lips comprising applying the composition of the invention to the skin or lips and allowing the formation of said protective layer.

In another embodiment the invention provides a method for coloring hair, eyebrows, skin or nails comprising applying the hair, eyebrows, skin or nail coloring composition of the invention to the hair, eyebrows, skin or nails for a period of time sufficient to cause coloration of the hair, eyebrows, skin or nails.

In a preferred embodiment the invention provides a method for coloring hair, eyebrows or eyelashes comprising the steps of:
a) providing a hair coloring composition comprising a hair colorant selected from the group consisting of:
    i) $(HBP)_n\text{-}C$; and
    ii) $[(HBP)_m\text{-}S]_k\text{-}C$
wherein
    1) HBP is a hair-binding peptide;
    2) C is a coloring agent;
    3) n ranges from 1 to about 10,000;
    4) S is a spacer;
    5) m ranges from 1 to about 50; and
    6) k ranges from 1 to about 10,000;
and wherein the hair binding peptide is selected by a method comprising the steps of:
    A) providing a library of combinatorial generated phage-peptides;
    B) contacting the library of (A) with a hair sample to form a reaction solution comprising:
        (i) phage-peptide-hair complex;
        (ii) unbound hair, and
        (iii) uncomplexed peptides;
    C) isolating the phage-peptide-hair complex of (B);
    D) eluting the weakly bound peptides from the peptide complex of (B);
    E) identifying the remaining bound phage-peptides either by using the polymerase chain reaction directly with the phage-peptide-hair complex remaining after step (D), or by infecting bacterial host cells directly with the phage-peptide-hair complex remaining after step (D), growing the infected cells in a suitable growth medium, and isolating and identifying the phage-peptides from the grown cells, wherein the phage-peptides are from about 7 to about 25 amino acids and have a binding affinity for hair, as measured as $MB_{50}$, equal to or less than $10^{-5}$ M; and
b) applying the hair colorant of (a) to hair, eyebrows or eyelashes for a time sufficient for the peptide-based colorant to bind to hair, eyebrows or eyelashes.

In another embodiment the invention provides a method for forming a protective layer of a peptide-based conditioner on hair comprising the steps of:
a) providing a hair care composition comprising a hair conditioner selected from the group consisting of:
    i) $(HBP)_n\text{-}HCA$; and
    ii) $[(HBP)_m\text{-}S]_k\text{-}HCA$
wherein
    1) HBP is a hair-binding peptide;
    2) HCA is a hair conditioning agent;
    3) n ranges from 1 to about 1,000;
    4) S is a spacer;
    5) m ranges from 1 to about 50; and
    6) k ranges from 1 to about 1,000;
and wherein the hair binding peptide is selected by a method comprising the steps of:
    A) providing a library of combinatorial generated phage-peptides;

B) contacting the library of (A) with a hair sample to form a reaction solution comprising:
(i) phage-peptide-hair complex;
(ii) unbound hair, and
(iii) uncomplexed peptides;
C) isolating the phage-peptide-hair complex of (B)
D) eluting the weakly bound peptides from the peptide complex of (B);
E) identifying the remaining bound phage-peptides either by using the polymerase chain reaction directly with the phage-peptide-hair complex remaining after step (D), or by infecting bacterial host cells directly with the phage-peptide-hair complex remaining after step (D), growing the infected cells in a suitable growth medium, and isolating and identifying the phage-peptides from the grown cells, wherein the phage-peptides are from about 7 to about 25 amino acids and have a binding affinity for hair, as measured as $MB_{50}$, equal to or less than $10^{-5}$ M; and
b) applying the hair conditioner of (a) to hair and allowing the formation of
said protective layer.

Alternatively the invention provides a method for forming a protective layer on skin or lips comprising the steps of:
a) providing a skin care composition comprising a skin conditioner selected from the group consisting of:
i) $(SBP)_n$-SCA; and
ii) $[(SBP)_m$-S$]_k$-SCA
wherein
1) SBP is a skin-binding peptide;
2) SCA is a skin conditioning agent;
3) n ranges from 1 to about 1,000;
4) S is a spacer;
5) m ranges from 1 to about 50; and
6) k ranges from 1 to about 1,000;
and wherein the skin binding peptide is selected by a method comprising the steps of:
A) providing a library of combinatorial generated phage-peptides;
B) contacting the library of (A) with a skin sample to form a reaction solution comprising:
(i) phage-peptide-skin complex;
(ii) unbound skin, and
(iii) uncomplexed peptides;
C) isolating the phage-peptide-skin complex of (B);
D) eluting the weakly bound peptides from the peptide complex of (B);
E) identifying the remaining bound phage-peptides either by using the polymerase chain reaction directly with the phage-peptide-skin complex remaining after step (D), or by infecting bacterial host cells directly with the phage-peptide-skin complex remaining after step (D), growing the infected cells in a suitable growth medium, and isolating and identifying the phage-peptides from the grown cells, wherein the phage-peptides are from about 7 to about 25 amino acids and have a binding affinity for skin, as measured as $MB_{50}$, equal to or less than $10^{-5}$ M; and
b) applying the skin conditioner of (a) to skin or lips and allowing the formation of said protective layer.

In another embodiment the invention provides a method for coloring skin or lips comprising the steps of:
a) providing a cosmetic composition comprising a skin colorant selected from the group consisting of:
i) $(SBP)_n$-C; and
ii) $[(SBP)_m$-S$]_k$-C
wherein
1) SBP is a skin-binding peptide;
2) C is a coloring agent;
3) n ranges from 1 to about 10,000;
4) S is a spacer;
5) m ranges from 1 to about 50; and
6) k ranges from 1 to about 10,000;
and wherein the skin binding peptide is selected by a method comprising the steps of:
A) providing a library of combinatorial generated phage-peptides;
B) contacting the library of (A) with a skin sample to form a reaction solution comprising:
(i) phage-peptide-skin complex;
(ii) unbound skin, and
(iii) uncomplexed peptides;
C) isolating the phage-peptide-skin complex of (B);
D) eluting the weakly bound peptides from the peptide complex of (B);
E) identifying the remaining bound phage-peptides either by using the polymerase chain reaction directly with the phage-peptide-skin complex remaining after step (D), or by infecting bacterial host cells directly with the phage-peptide-skin complex remaining after step (D), growing the infected cells in a suitable growth medium, and isolating and identifying the phage-peptides from the grown cells, wherein the phage-peptides are from about 7 to about 25 amino acids and have a binding affinity for skin, as measured as $MB_{50}$, equal to or less than $10^{-5}$ M; and
b) applying the skin colorant of (a) to the skin or lips.

Alternatively the invention provides a method for coloring nails comprising the steps of:
a) providing a nail polish composition comprising a nail colorant selected from the group consisting of:
i) $(NBP)_n$-C; and
ii) $[(NBP)_m$-S$]_k$-C
wherein
1) NBP is a nail-binding peptide;
2) C is a coloring agent;
3) n ranges from 1 to about 10,000;
4) S is a spacer;
5) m ranges from 1 to about 50; and
6) k ranges from 1 to about 10,000;
and wherein the nail binding peptide is selected by a method comprising the steps of:
A) providing a library of combinatorial generated phage-peptides;
B) contacting the library of (A) with a nail sample to form a reaction solution comprising:
(i) phage-peptide-nail complex;
(ii) unbound nail, and
(iii) uncomplexed peptides;
C) isolating the phage-peptide-nail complex of (B);
D) eluting the weakly bound peptides from the peptide complex of (B);
E) identifying the remaining bound phage-peptides either by using the polymerase chain reaction directly with the phage-peptide-nail complex remaining after step (D), or by infecting bacterial host cells directly with the phage-peptide-nail complex remaining after step (D), growing the infected cells in a suitable growth medium, and isolating and identifying the phage-peptides from the grown cells, wherein the phage-peptides are from about 7 to about 25 amino acids and have a binding affinity for nails, as measured as $MB_{50}$, equal to or less than $10^{-5}$ M; and b) applying the nail colorant of (a) to the nails.

BRIEF DESCRIPTION OF SEQUENCE DESCRIPTIONS

The invention can be more fully understood from the following detailed description and the accompanying sequence descriptions, which form a part of this application.

The following sequences conform with 37 C.F.R. 1.821-1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 is the amino acid sequence of a hair-binding peptide.

SEQ ID NO:2 is the amino acid sequence of a skin-binding peptide.

SEQ ID NOs:3-52, 54-59 are the amino acid sequences of hair-binding peptides of the present invention SEQ ID NO:53 is the amino acid sequence of a hair-binding and nail-binding peptide of the present invention.

SEQ ID NO:60 is the amino acid sequence of a nail-binding peptide of the present invention.

SEQ ID NO:61 is the amino acid sequence of a skin-binding peptide of the present invention.

SEQ ID NO:62 is the oligonucleotide primer used to sequence phage DNA.

SEQ ID NO:63 is the amino acid sequence of a peptide used as a control in the ELISA binding assay.

SEQ ID NO:64 is the amino acid sequence of a cysteine-attached hair-binding peptide.

SEQ ID NO:65 is the amino acid sequence of the Caspase 3 cleavage site.

SEQ ID NOs:66, 69, and 70 are the amino acid sequence of shampoo-resistant hair-binding peptides.

SEQ ID NOs:67 and 68 are the nucleotide sequences of the primers used to amplify shampoo-resistant, hair-binding phage peptides, as described in Example 8.

SEQ ID NOs:71-74 are the amino acid sequences of the biotinylated hair-binding and skin-binding peptides used Example 9.

SEQ ID NO:75 is the amino acid sequence of the fully protected D21 peptide used in Example 16.

SEQ ID NOs:76-98 are the amino acid sequences of hair-binding peptides.

SEQ ID NOs:99-104 are the amino acid sequences of skin-binding peptides.

DETAILED DESCRIPTION OF THE INVENTION

The present invention provides peptide sequences that specifically bind to human hair, skin, and nails with high affinity. Additionally, the present invention provides peptide-based hair and skin conditioners, and hair, nail, and skin colorants with improved durability.

The following definitions are used herein and should be referred to for interpretation of the claims and the specification.

"HBP" means hair-binding peptide.
"SBP" means skin-binding peptide.
"NBP" means nail-binding peptide.
"HCA" means hair conditioning agent.

"SCA" means skin conditioning agent.
"C" means coloring agent for hair, skin, or nails.
"S" means spacer.

The term "peptide" refers to two or more amino acids joined to each other by peptide bonds or modified peptide bonds.

The term "hair" as used herein refers to human hair, eyebrows, and eyelashes.

The term "skin" as used herein refers to human skin, or pig skin, Vitro-Skin® and EpiDerm™ which are substitutes for human skin.

The term "nails" as used herein refers to human fingernails and toenails.

The term "stringency" as it is applied to the selection of the hair-binding, skin-binding, and nail-binding peptides of the present invention, refers to the concentration of the eluting agent (usually detergent) used to elute peptides from the hair, skin, or nails. Higher concentrations of the eluting agent provide more stringent conditions.

The term "peptide-hair complex" means structure comprising a peptide bound to a hair fiber via a binding site on the peptide.

The term "peptide-skin complex" means structure comprising a peptide bound to the skin via a binding site on the peptide.

The term "peptide-nail complex" means structure comprising a peptide bound to fingernails or toenails via a binding site on the peptide.

The term "peptide-substrate complex" refers to either peptide-hair, peptide-skin, or peptide-nail complexes.

The term "$MB_{50}$" refers to the concentration of the binding peptide that gives a signal that is 50% of the maximum signal obtained in an ELISA-based binding assay, as described in Example 9. The $MB_{50}$ provides an indication of the strength of the binding interaction or affinity of the components of the complex. The lower the value of $MB_{50}$, the stronger the interaction of the peptide with its corresponding substrate.

The term "binding affinity" refers to the strength of the interaction of a binding peptide with its respective substrate. The binding affinity is defined herein in terms of the $MB_{50}$ value, determined in an ELISA-based binding assay.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" gene refers to a gene not normally found in the host organism, but that is introduced into the host organism by gene transfer. Foreign genes can comprise native genes inserted into a non-native organism, or chimeric genes.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "expression", as used herein, refers to the transcription and stable accumulation of sense (mRNA) or anti-sense RNA derived from the nucleic acid fragment of the invention. Expression may also refer to translation of mRNA into a polypeptide.

The term "transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The term "host cell" refers to cell which has been transformed or transfected, or is capable of transformation or transfection by an exogenous polynucleotide sequence.

The terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "phage" or "bacteriophage" refers to a virus that infects bacteria. Altered forms may be used for the purpose of the present invention. The preferred bacteriophage is derived from the "wild" phage, called M13. The M13 system can grow inside a bacterium, so that it does not destroy the cell it infects but causes it to make new phages continuously. It is a single-stranded DNA phage.

The term "phage display" refers to the display of functional foreign peptides or small proteins on the surface of bacteriophage or phagemid particles. Genetically engineered phage may be used to present peptides as segments of their native surface proteins. Peptide libraries may be produced by populations of phage with different gene sequences.

"PCR" or "polymerase chain reaction" is a technique used for the amplification of specific DNA segments (U.S. Pat. Nos. 4,683,195 and 4,800,159).

Standard recombinant DNA and molecular cloning techniques used herein are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

The present invention comprises specific hair-binding, skin-binding, and nail-binding peptides and their use in conditioners and coloring agents for the hair, skin, and nails.

Hair, Skin, and Nails

Human hair samples are available commercially, for example from International Hair Importers and Products (Bellerose, N.Y.), in different colors, such as brown, black, red, and blond, and in various types, such as African-American, Caucasian, and Asian. Additionally, the hair samples may be treated for example using hydrogen peroxide to obtain bleached hair. Pig skin, available from butcher shops and supermarkets, Vitro-Skin®, available from IMS Inc. (Milford, Conn.), and EpiDerm™, available from MatTek Corp. (Ashland, Mass.), are good substitutes for human skin. Human fingernails and toenails may be obtained from volunteers.

Hair-Binding, Skin-Binding, and Nail-Binding Peptides

Hair-binding peptides (HBPs), skin-binding peptides (SBPs) and nail-binding peptides (NBPs) as defined herein are peptide sequences that specifically bind with high affinity to hair, skin and nails, respectively. The hair-binding, skin-binding, and nail-binding peptides of the present invention are from about 7 amino acids to about 45 amino acids, more preferably, from about 7 amino acids to about 20 amino acids, most preferably from about 7 to about 12 amino acids. The binding peptides of the invention have a binding affinity for their respective substrate, as measured by $MB_{50}$ values, of less than or equal to about $10^{-2}$ M, less than or equal to about $10^{-3}$ M, less than or equal to about $10^{-4}$ M, less than or equal to about $10^{-5}$ M, preferably less than or equal to about $10^{-6}$ M, and more preferably less than or equal to about $10^{-7}$ M.

Suitable hair-binding, skin-binding, and nail-binding peptide sequences may be selected using methods that are well known in the art. The peptides of the present invention are generated randomly and then selected against a specific hair, skin, or nail sample based upon their binding affinity for the substrate of interest. The generation of random libraries of peptides is well known and may be accomplished by a variety of techniques including, bacterial display (Kemp, D. J.; *Proc. Natl. Acad. Sci. USA* 78(7):4520-4524 (1981), and Helfman et al., *Proc. Natl. Acad. Sci. USA* 80(1):31-35, (1983)), yeast display (Chien et al., *Proc Natl Acad Sci USA* 88(21):9578-82 (1991)), combinatorial solid phase peptide synthesis (U.S. Pat. No. 5,449,754, U.S. Pat. No. 5,480,971, U.S. Pat. No. 5,585,275, U.S. Pat. No. 5,639,603), and phage display technology (U.S. Pat. No. 5,223,409, U.S. Pat. No. 5,403,484, U.S. Pat. No. 5,571,698, U.S. Pat. No. 5,837,500). Techniques to generate such biological peptide libraries are described in Dani, M., *J. of Receptor & Signal Transduction Res.*, 21 (4):447-468 (2001).

A preferred method to randomly generate peptides is by phage display. Phage display is an in vitro selection technique in which a peptide or protein is genetically fused to a coat protein of a bacteriophage, resulting in display of fused peptide on the exterior of the phage virion, while the DNA encoding the fusion resides within the virion. This physical linkage between the displayed peptide and the DNA encoding it allows screening of vast numbers of variants of peptides, each linked to a corresponding DNA sequence, by a simple in vitro selection procedure called "biopanning". In its simplest form, biopanning is carried out by incubating the pool of phage-displayed variants with a target of interest that has been immobilized on a plate or bead, washing away unbound phage, and eluting specifically bound phage by disrupting the binding interactions between the phage and the target. The eluted phage is then amplified in vivo and the process is repeated, resulting in a stepwise enrichment of the phage pool in favor of the tightest binding sequences. After 3 or more rounds of selection/amplification, individual clones are characterized by DNA sequencing.

After a suitable library of peptides has been generated, they are then contacted with an appropriate amount of the test substrate, specifically a hair, skin, or nail sample. The test substrate is presented to the library of peptides while suspended in solution. A preferred solution is a buffered aqueous saline solution containing a surfactant. A suitable solution is Tris-buffered saline (TBS) with 0.5% Tween® 20. The solution may additionally be agitated by any means in order to increase the mass transfer rate of the peptides to the hair, skin, or nail surface, thereby shortening the time required to attain maximum binding.

Upon contact, a number of the randomly generated peptides will bind to the hair, skin, or nail substrate to form a peptide-hair, peptide-skin or peptide-nail complex. Unbound peptide may be removed by washing. After all unbound material is removed, peptides having varying degrees of binding affinities for the test substrate may be fractionated by selected washings in buffers having varying stringencies. Increasing the stringency of the buffer used increases the required strength of the bond between the peptide and substrate in the peptide-substrate complex.

A number of substances may be used to vary the stringency of the buffer solution in peptide selection including, but not limited to, acidic pH (1.5-3.0); basic pH (10-12.5); high salt concentrations such as $MgCl_2$ (3-5 M) and LiCl (5-10 M); water; ethylene glycol (25-50%); dioxane (5-20%); thiocyanate (1-5 M); guanidine (2-5 M); urea (2-8 M); and various concentrations of different surfactants such as SDS (sodium dodecyl sulfate), DOC (sodium deoxycholate), Nonidet P40, Triton X-100, Tween® 20, wherein Tween® 20 is preferred. These substances may be prepared in buffer solutions including, but not limited to, Tris-HCl, Tris-buffered saline, Tris-borate, Tris-acetic acid, triethylamine, phosphate buffer, and glycine-HCl, wherein Tris-buffered saline solution is preferred.

It will be appreciated that peptides having increasing binding affinities for hair, skin or nail substrates may be eluted by repeating the selection process using buffers with increasing stringencies. The eluted peptides can be identified and sequenced by any means known in the art.

Thus, the following method for generating the hair-binding peptides, skin-binding peptides, or nail-binding peptides of the present invention was used. A library of combinatorial generated phage-peptides is contacted with the substrate of interest, specifically, a hair, skin, or nail sample, to form phage-peptide-hair, phage-peptide-skin, or phage-peptide-nail complexes. The phage-peptide-substrate complex is separated from uncomplexed peptides and unbound substrate, and the bound phage-peptides from the phage-peptide-substrate complexes is eluted from the complex, preferably by acid treatment. Then, the eluted peptides are identified and sequenced. To identify peptide sequences that bind to one substrate but not to another, for example peptides that bind to hair, but not to skin or peptides that bind to skin, but not to hair, a subtractive panning step is added. Specifically, the library of combinatorial generated phage-peptides is first contacted with the non-target to remove phage-peptides that bind to it. Then, the non-binding phage-peptides are contacted with the desired substrate and the above process is followed. Alternatively, the library of combinatorial generated phage-peptides may be contacted with the non-target and the desired substrate simultaneously. Then, the phage-peptide-substrate complexes are separated from the phage-peptide-non-target complexes and the method described above is followed for the desired phage-peptide-substrate complexes.

One embodiment of the present invention provides a modified phage display screening method for isolating peptides with a higher affinity for hair, skin, or nails. In the modified method, the phage-peptide-substrate complexes are formed as described above. Then, these complexes are treated with an elution buffer. Any of the elution buffers described above may be used. Preferably, the elution buffer is an acidic solution. Then, the remaining, elution-resistant phage-peptide-substrate complexes are used to directly infect a bacterial host cell, such as *E. coli* ER2738. The infected host cells are grown in an appropriate growth medium, such as LB (Luria-Bertani) medium, and this culture is spread onto agar, containing a suitable growth medium, such as LB medium with IPTG (isopropyl β-D-thiogalactopyranoside) and S-Gal™. After growth, the plaques are picked for DNA isolation and sequencing to identify the peptide sequences with a high binding affinity for the hair, skin, or nail substrate.

In another embodiment, PCR may be used to identify the elution-resistant phage-peptides from the modified phage display screening method, described above, by directly carrying out PCR on the phage-peptide-substrate complexes using the appropriate primers, as described by Janssen et al. in U.S. Patent Application Publication No. 2003/0152976, which is incorporated herein by reference.

Hair-binding, skin-binding, and nail-binding peptides have been identified using the above methods. Specifically, binding peptides were isolated that have a high affinity for normal brown hair, given as SEQ ID NOs:3-18, 28-38, 40-56, and 64; shampoo resistant, normal brown hair, given as SEQ ID NO:66, 69 and 70; bleached hair, given as SEQ ID NOs:7, 8, 19-27, 38-40, 43, 44, 47, 57, 58, and 59, fingernail, given as SEQ ID NOs:53 and 60; and skin, given as SEQ ID NO:61. Additionally, the fingernail-binding peptides were found to bind to bleached hair and may be used in the peptide-based hair conditioners and hair colorants of the invention. The bleached hair-binding peptides will bind to fingernails and may be used in the peptide-based nail colorants of the invention.

Production of Binding Peptides

The binding peptides of the present invention may be prepared using standard peptide synthesis methods, which are well known in the art (see for example Stewart et al., *Solid Phase Peptide Synthesis*, Pierce Chemical Co., Rockford, Ill., 1984; Bodanszky, *Principles of Peptide Synthesis*, Springer-Verlag, New York, 1984; and Pennington et al., *Peptide Synthesis Protocols*, Humana Press, Totowa, N.J., 1994). Additionally, many companies offer custom peptide synthesis services.

Alternatively, the peptides of the present invention may be prepared using recombinant DNA and molecular cloning techniques. Genes encoding the hair-binding, skin-binding or nail-binding peptides may be produced in heterologous host cells, particularly in the cells of microbial hosts.

Preferred heterologous host cells for expression of the binding peptides of the present invention are microbial hosts that can be found broadly within the fungal or bacterial families and which grow over a wide range of temperature, pH values, and solvent tolerances. Because transcription, translation, and the protein biosynthetic apparatus are the same irrespective of the cellular feedstock, functional genes are expressed irrespective of carbon feedstock used to generate cellular biomass. Examples of host strains include, but are not limited to, fungal or yeast species such as *Aspergillus, Trichoderma, Saccharomyces, Pichia, Candida, Hansenula*, or bacterial species such as *Salmonella, Bacillus, Acinetobacter, Rhodococcus, Streptomyces, Escherichia, Pseudomonas, Methylomonas, Methylobacter, Alcaligenes, Synechocystis, Anabaena, Thiobacillus, Methanobacterium* and *Klebsiella*.

A variety of expression systems can be used to produce the peptides of the present invention. Such vectors include, but are not limited to, chromosomal, episomal and virus-derived vectors, e.g., vectors derived from bacterial plasmids, from bacteriophage, from transposons, from insertion elements, from yeast episoms, from viruses such as baculoviruses, retroviruses and vectors derived from combinations thereof such as those derived from plasmid and bacteriophage genetic elements, such as cosmids and phagemids. The expression system constructs may contain regulatory regions that regulate as well as engender expression. In general, any system or vector suitable to maintain, propagate or express polynucleotide or polypeptide in a host cell may be used for expression in this regard. Microbial expression systems and expression vectors contain regulatory sequences that direct high level expression of foreign proteins relative to the growth of the host cell. Regulatory sequences are well known to those skilled in the art and examples include, but are not limited to, those which cause the expression of a gene to be turned on or off in response to a chemical or physical stimulus, including the presence of regulatory elements in the vector, for example, enhancer sequences. Any of these could be used to construct chimeric genes for production of the any of the binding peptides of the present invention. These chimeric genes could then be introduced into appropriate microorganisms via transformation to provide high level expression of the peptides.

Vectors or cassettes useful for the transformation of suitable host cells are well known in the art. Typically the vector or cassette contains sequences directing transcription and translation of the relevant gene, one or more selectable markers, and sequences allowing autonomous replication or chromosomal integration. Suitable vectors comprise a region 5' of the gene, which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host. Selectable marker genes provide a phenotypic trait for selection of the transformed host cells such as tetracycline or ampicillin resistance in *E. coli*.

Initiation control regions or promoters which are useful to drive expression of the chimeric gene in the desired host cell are numerous and familiar to those skilled in the art. Virtually any promoter capable of driving the gene is suitable for producing the binding peptides of the present invention including, but not limited to: CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara, tet, trp, $IP_L$, $IP_R$, T7, tac, and trc (useful for expression in *Escherichia coli*) as well as the amy, apr, npr promoters and various phage promoters useful for expression in *Bacillus*.

Termination control regions may also be derived from various genes native to the preferred hosts. Optionally, a termination site may be unnecessary, however, it is most preferred if included.

The vector containing the appropriate DNA sequence as described supra, as well as an appropriate promoter or control sequence, may be employed to transform an appropriate host to permit the host to express the peptide of the present invention. Cell-free translation systems can also be employed to produce such peptides using RNAs derived from the DNA constructs of the present invention. Optionally it may be desired to produce the instant gene product as a secretion product of the transformed host. Secretion of desired proteins into the growth media has the advantages of simplified and less costly purification procedures. It is well known in the art that secretion signal sequences are often useful in facilitating the active transport of expressible proteins across cell membranes. The creation of a transformed host capable of secretion may be accomplished by the incorporation of a DNA sequence that codes for a secretion signal which is functional in the production host. Methods for choosing appropriate signal sequences are well known in the art (see for example EP 546049 and WO 9324631). The secretion signal DNA or facilitator may be located between the expression-controlling DNA and the instant gene or gene fragment, and in the same reading frame with the latter.

Peptide-Based Hair Conditioners

The peptide-based hair conditioners of the present invention are formed by coupling a hair-binding peptide (HBP) with a hair conditioning agent (HCA). The hair-binding peptide part of the conditioner binds strongly to the hair, thus keeping the conditioning agent attached to the hair for a long lasting conditioning effect. The hair-binding peptides include, but are not limited to, hair-binding peptides selected by the screening methods described above, including the hair-binding peptide sequences of the invention, given by SEQ ID NOs: 3-59, 64, 66, 69, and 70, most preferably the peptides given by SEQ ID NO:46 and SEQ ID NO:66, which bind strongly to hair, but not to skin. Additionally, any known hair-binding peptide may be used, including but not limited to SEQ ID NO:1, and SEQ ID NOs:76-98, described by Janssen et al. in U.S. Patent Application Publication No. 2003/0152976 and by Janssen et al. in WO 04048399, respectively, both of which are incorporated herein by reference. For bleached hair, the fingernail-binding peptide, given as SEQ ID NO:60, may also be used.

Hair conditioning agents as herein defined are agents which improve the appearance, texture, and sheen of hair as well as increasing hair body or suppleness. In the peptide-based hair conditioners of the present invention, any known hair conditioning agent may be used. Hair conditioning agents are well known in the art, see for example Green et al. (WO 0107009), incorporated herein by reference, and are available commercially from various sources. Suitable examples of hair conditioning agents include, but are not limited to, cationic polymers, such as cationized guar gum, diallyly quaternary ammonium salt/acrylamide copolymers, quaternized polyvinylpyrrolidone and derivatives thereof, and various polyquaternium-compounds; cationic surfactants, such as stearalkonium chloride, centrimonium chloride, and Sapamin hydrochloride; fatty alcohols, such as behenyl alcohol; fatty amines, such as stearyl amine; waxes; esters; nonionic polymers, such as polyvinylpyrrolidone, polyvinyl alcohol, and polyethylene glycol; silicones; siloxanes, such as decamethylcyclopentasiloxane; polymer emulsions, such as amodimethicone; and voluminizing agents, such as for example chitosan. The preferred hair conditioning agents of the present invention contain amine or hydroxyl functional groups to facilitate coupling to the hair-binding peptides, as described below. Examples of preferred conditioning agents are octylamine (CAS No. 111-86-4), stearyl amine (CAS No. 124-30-1), behenyl alcohol (CAS No. 661-19-8, Cognis Corp., Cincinnati, Ohio), vinyl group terminated siloxanes, vinyl group terminated silicone (CAS No. 68083-19-2), vinyl group terminated methyl vinyl siloxanes, vinyl group terminated methyl vinyl silicone (CAS No. 68951-99-5), hydroxyl terminated siloxanes, hydroxyl terminated silicone (CAS No. 80801-30-5), amino-modified silicone derivatives, [(aminoethyl)amino]propyl hydroxyl dimethyl siloxanes, [(aminoethyl)amino]propyl hydroxyl dimethyl silicones, and alpha-tridecyl-omega-hydroxy-poly(oxy-1,2-ethanediyl) (CAS No. 24938-91-8).

The peptide-based hair conditioners of the present invention are prepared by covalently attaching a specific hair-binding peptide to a hair conditioning agent, either directly or via a spacer. Any known peptide or protein conjugation chemistry may be used to form the peptide-based hair conditioners of the present invention. Conjugation chemistries are well-known in the art (see for example, Hermanson, *Bioconjugate Techniques*, Academic Press, New York (1996)). Suitable coupling agents include, but are not limited to, carbodiimide coupling agents, diacid chlorides, diisocyanates and other difunctional coupling reagents that are reactive toward terminal amine and/or carboxylic acid terminal groups on the peptides and to amine, carboxylic acid, or alcohol groups on the hair conditioning agent. The preferred coupling agents are carbodiimide coupling agents, such as 1-ethyl-3-(3-dimethylaminopropyl)-carbodiimide (EDC) and N,N'-dicyclohexyl-carbodiimide (DCC), which may be used to activate carboxylic acid groups for coupling to alcohol, and amine groups. Additionally, it may be necessary to protect reactive amine or carboxylic acid groups on the peptide to produce the desired structure for the peptide-based hair conditioner. The use of protecting groups for amino acids, such as t-butyloxycarbonyl (t-Boc), are well known in the art (see for example Stewart et al., supra; Bodanszky, supra; and Pennington et al., supra). In some cases it may be necessary to introduce reactive groups, such as carboxylic acid, alcohol, amine, or aldehyde groups, on the hair conditioning agent for coupling to the hair-binding peptide. These modifications may be done using routine chemistry such as oxidation, reduction and the like, which is well known in the art.

It may also be desirable to couple the hair-binding peptide to the hair conditioning agent via a spacer. The spacer serves to separate the conditioning agent from the peptide to ensure that the agent does not interfere with the binding of the peptide to the hair. The spacer may be any of a variety of molecules, such as alkyl chains, phenyl compounds, ethylene glycol, amides, esters and the like. Preferred spacers are hydrophilic and have a chain length from 1 to about 100 atoms, more preferably, from 2 to about 30 atoms. Examples of preferred spacers include, but are not limited to ethanol amine, ethylene glycol, polyethylene with a chain length of 6 carbon atoms, polyethylene glycol with 3 to 6 repeating units, phenoxyethanol, propanolamide, butylene glycol, butyleneglycolamide, propyl phenyl, and ethyl, propyl, hexyl, steryl, cetyl, and palmitoyl alkyl chains. The spacer may be covalently attached to the peptide and the hair conditioning agent using any of the coupling chemistries described above. In order to facilitate incorporation of the spacer, a bifunctional cross-linking agent that contains a spacer and reactive groups at both ends for coupling to the peptide and the conditioning agent may be used. Suitable bifunctional cross-linking agents are well known in the art and include, but are not limited to diamines, such a as 1,6-diaminohexane; dialdehydes, such as glutaraldehyde; bis N-hydroxysuccinimide esters, such as ethylene glycol-bis(succinic acid N-hydroxysuccinimide ester), disuccinimidyl glutarate, disuccinimidyl suberate, and ethylene glycol-bis(succinimidylsuccinate); diisocyantes, such as hexamethylenediisocyanate; bis oxiranes, such as 1,4 butanediyl diglycidyl ether; dicarboxylic acids, such as succinyldisalicylate; and the like. Heterobifunctional cross-linking agents, which contain a different reactive group at each end, may also be used. Examples of heterobifunctional cross-linking agents include, but are not limited to compounds having the following structure:

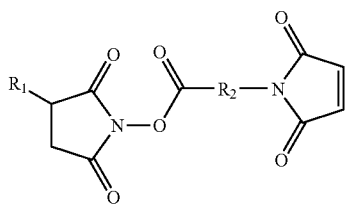

where: $R_1$ is H or a substituent group such as —$SO_3Na$, —$NO_2$, or —Br; and $R_2$ is a spacer such as —$CH_2CH_2$ (ethyl), —$(CH_2)_3$ (propyl), or —$(CH_2)_3C_6H_5$ (propyl phenyl). An example of such a heterobifunctional cross-linking agent is 3-maleimidopropionic acid N-hydroxysuccinimide ester. The N-hydroxysuccinimide ester group of these reagents reacts with amine or alcohol groups on the conditioner, while the maleimide group reacts with thiol groups present on the peptide. A thiol group may be incorporated into the peptide by adding a cysteine group to at least one end of the binding peptide sequence. Several spacer amino acid residues, such as glycine, may be incorporated between the binding peptide sequence and the terminal cysteine to separate the reacting thiol group from the binding sequence.

Additionally, the spacer may be a peptide composed of any amino acid and mixtures thereof. The preferred peptide spacers are composed of the amino acids glycine, alanine, and serine, and mixtures thereof. In addition, the peptide spacer may contain a specific enzyme cleavage site, such as the protease Caspase 3 site, given by SEQ ID NO:65, which allows for the enzymatic removal of the conditioning agent from the hair. The peptide spacer may be from 1 to about 50 amino acids, preferably from 1 to about 20 amino acids. These peptide spacers may be linked to the binding peptide sequence by any method know in the art. For example, the entire binding peptide-peptide spacer diblock may be prepared using the standard peptide synthesis methods described supra. In addition, the binding peptide and peptide spacer blocks may be combined using carbodiimide coupling agents (see for example, Hermanson, *Bioconjugate Techniques*, Academic Press, New York (1996)), diacid chlorides, diisocyanates and other difunctional coupling reagents that are reactive to terminal amine and/or carboxylic acid terminal groups on the peptides. Alternatively, the entire binding peptide-peptide spacer diblock may be prepared using the recombinant DNA and molecular cloning techniques described supra. The spacer may also be a combination of a peptide spacer and an organic spacer molecule, which may be prepared using the methods described above.

It may also be desirable to have multiple hair-binding peptides attached to the hair conditioning agent to enhance the interaction between the peptide-based hair conditioner and the hair. Either multiple copies of the same hair-binding peptide or a combination of different hair-binding peptides may be used. In the case of large conditioning particles (e.g., particle emulsions), a large number of hair-binding peptides, i.e., up to about 1,000, may be attached to the conditioning agent. A smaller number of hair-binding peptides can be attached to the smaller conditioner molecules, i.e., up to about 50. Therefore, in one embodiment of the present invention, the peptide-based hair conditioners are diblock compositions consisting of a hair-binding peptide (HBP) and a hair conditioning agent (HCA), having the general structure $(HBP)_n$-HCA, where n ranges from 1 to about 1,000, preferably from 1 to about 50.

In another embodiment, the peptide-based hair conditioners contain a spacer (S) separating the hair-binding peptide from the hair conditioning agent, as described above. Multiple copies of the hair-binding peptide may be attached to a single spacer molecule. In this embodiment, the peptide-based hair conditioners are triblock compositions consisting of a hair-binding peptide, a spacer, and a hair conditioning agent, having the general structure $[(HBP)_m\text{-}S]_n$-HCA, where n ranges from 1 to about 1,000, preferably n is 1 to about 50, and m ranges from 1 to about 50, preferably m is 1 to about 10.

The peptide-based hair conditioners of the present invention may be used in compositions for hair care. It should also be recognized that the hair-binding peptides themselves can serve as conditioning agents for the treatment of hair. Hair care compositions are herein defined as compositions for the treatment of hair, including but not limited to shampoos, conditioners, lotions, aerosols, gels, mousses, and hair dyes comprising an effective amount of a peptide-based hair conditioner or a mixture of different peptide-based hair conditioners in a cosmetically acceptable medium. An effective amount of a peptide-based hair conditioner or hair-binding peptide for use in a hair care composition is herein defined as a proportion of from about 0.01% to about 10%, preferably about 0.01% to about 5% by weight relative to the total weight of the composition. Components of a cosmetically acceptable medium for hair care compositions are described by Philippe et al. in U.S. Pat. No. 6,280,747, and by Omura et al. in U.S. Pat. No. 6,139,851 and Cannell et al. in U.S. Pat. No. 6,013,250, all of which are incorporated herein by reference. For example, these hair care compositions can be aqueous, alcoholic or aqueous-alcoholic solutions, the alcohol preferably being ethanol or isopropanol, in a proportion of from about 1 to about 75% by weight relative to the total weight, for the aqueous-alcoholic solutions. Additionally, the hare care compositions may contain one or more conventional cosmetic or dermatological additives or adjuvants including but not limited to, antioxidants, preserving agents, fillers, surfactants, UVA and/or UVB sunscreens, fragrances, thickeners, wetting agents and anionic, nonionic or amphoteric polymers, and dyes or pigments.

Peptide-Based Skin Conditioners

The peptide-based skin conditioners of the present invention are formed by coupling a skin-binding peptide (SBP) with a skin conditioning agent (SCA). The skin-binding peptide part of the conditioner binds strongly to the skin, thus keeping the conditioning agent attached to the skin for a long lasting conditioning effect. The skin-binding peptides include, but are not limited to, skin-binding peptides selected by the screening methods described above, including the skin-binding peptide sequence of the invention, given as SEQ ID NO:61. Additionally, any known skin-binding peptide may be used, including but not limited to SEQ ID NO:2, and SEQ ID NOs:99-104, described by Janssen et al. in U.S. Patent Application Publication No. 2003/0152976 and by Janssen et al. in WO 04048399, respectively.

Skin conditioning agents as herein defined include, but are not limited to astringents, which tighten skin; exfoliants, which remove dead skin cells; emollients, which help maintain a smooth, soft, pliable appearance; humectants, which increase the water content of the top layer of skin; occlusives, which retard evaporation of water from the skin's surface; and miscellaneous compounds that enhance the appearance of dry or damaged skin or reduce flaking and restore suppleness. In the peptide-based skin conditioners of the present invention, any known skin conditioning agent may be used. Skin conditioning agents are well known in the art, see for example Green et al. supra, and are available commercially from various sources. Suitable examples of skin conditioning agents include, but are not limited to, alpha-hydroxy acids, beta-hydroxy acids, polyols, hyaluronic acid, D,L-panthenol, polysalicylates, vitamin A palmitate, vitamin E acetate, glycerin, sorbitol, silicones, silicone derivatives, lanolin, natural oils and triglyceride esters. The preferred skin conditioning agents of the present invention are polysalicylates, propylene glycol (CAS No. 57-55-6, Dow Chemical, Midland, Mich.), glycerin (CAS No. 56-81-5, Proctor & Gamble Co., Cincinnati, Ohio), glycolic acid (CAS No. 79-14-1, DuPont Co., Wilmington, Del.), lactic acid (CAS No. 50-21-5, Alfa Aesar, Ward Hill, Mass.), malic acid (CAS No. 61748-1, Alfa Aesar), citric acid (CAS No. 77-92-9, Alfa Aesar), tartaric acid (CAS NO. 133-37-9, Alfa Aesar), glucaric acid (CAS No. 87-73-0), galactaric acid (CAS No. 526-99-8), 3-hydroxyvaleric acid (CAS No. 10237-77-1), salicylic acid (CAS No. 69-72-7, Alfa Aesar), and 1,3 propanediol (CAS No. 504-63-2, DuPont Co., Wilmington, Del.). Polysalicylates may be prepared by the method described by White et al. in U.S. Pat. No. 4,855,483, incorporated herein by reference. Glucaric acid may be synthesized using the method described by Merbouh et al. (*Carbohydr. Res.* 336:75-78 (2001). The 3-hydroxyvaleric acid may be prepared as described by Bramucci in WO 02012530.

The peptide-based skin conditioners of the present invention are prepared by covalently attaching a specific skin-binding peptide to the skin conditioning agent, either directly or via a spacer. Any of the coupling methods described above may be used. It may be necessary to introduce reactive groups, such as carboxylic acid, alcohol, amine, or aldehyde groups, on the skin conditioning agent for coupling to the hair-binding peptide, as described above. It may also be desirable to have multiple skin-binding peptides attached to the skin conditioning agent to enhance the interaction between the peptide-based skin conditioner and the skin. Either multiple copies of the same skin-binding peptide or a combination of different skin-binding peptides may be used. In the case of large conditioning particles, a large number of skin-binding peptides, i.e., up to about 1,000, may be attached to the conditioning agent. A smaller number of skin-binding peptides can be attached to the smaller conditioner molecules, i.e., up to about 50. Therefore, in one embodiment of the present invention, the peptide-based skin conditioners are diblock compositions consisting of a skin-binding peptide (SBP) and a skin conditioning agent (SCA), having the general structure $(SBP)_n$-SCA, where n ranges from 1 to about 1,000, preferably from 1 to about 50.

In another embodiment, the peptide-based skin conditioners contain a spacer (S) separating the skin-binding peptide from the skin conditioning agent, as described above. Multiple copies of the skin-binding peptide may be attached to a single spacer molecule. In this embodiment, the peptide-based skin conditioners are triblock compositions consisting of a skin binding peptide, a spacer, and a skin conditioning agent, having the general structure $[(SBP)_m$-$S]_n$-SCA, where n ranges from 1 to about 1,000, preferably n is 1 to about 50, and m ranges from 1 to about 50, preferably m is 1 to about 10.

The peptide-based skin conditioners of the present invention may be used in compositions for skin care. It should also be recognized that the skin-binding peptides themselves can serve as conditioning agents for skin. Skin care compositions are herein defined as compositions comprising an effective amount of a peptide-based skin conditioner or a mixture of different peptide-based skin conditioners in a cosmetically acceptable medium. The uses of these compositions include, but are not limited to, skin care, skin cleansing, make-up, and anti-wrinkle products. An effective amount of a peptide-based skin conditioner or skin-binding peptide for skin care compositions is herein defined as a proportion of from about 0.001% to about 10%, preferably about 0.01% to about 5% by weight relative to the total weight of the composition. This proportion may vary as a function of the type of skin care composition. Suitable compositions for a cosmetically acceptable medium are described by Philippe et al. supra. For example, the cosmetically acceptable medium may be an anhydrous composition containing a fatty substance in a proportion generally of from about 10 to about 90% by weight relative to the total weight of the composition, where the fatty phase containing at least one liquid, solid or semi-solid fatty substance. The fatty substance includes, but is not limited to, oils, waxes, gums, and so-called pasty fatty substances. Alternatively, the compositions may be in the form of a stable dispersion such as a water-in-oil or oil-in-water emulsion. Additionally, the compositions may contain one or more conventional cosmetic or dermatological additives or adjuvants, including but not limited to, antioxidants, preserving agents, fillers, surfactants, UVA and/or UVB sunscreens, fragrances, thickeners, wetting agents and anionic, nonionic or amphoteric polymers, and dyes or pigments.

Peptide-Based Hair Colorants

The peptide-based hair colorants of the present invention are formed by coupling a hair-binding peptide (HBP) with a coloring agent (C). The hair-binding peptide part of the peptide-based hair colorant binds strongly to the hair, thus keeping the coloring agent attached to the hair for a long lasting hair coloring effect. The hair-binding peptides include, but are not limited to, hair-binding peptides selected by the screening methods described above, including the hair-binding peptide sequences of the invention, given by SEQ ID NOs: 3-59, 64, 66, 69 and 70, most preferably the peptides given by SEQ ID NO:46 and SEQ ID NO:66, which bind strongly to hair, but not to skin. Additionally, any known hair-binding peptide may be used, including but not limited to SEQ ID NO:1, and SEQ ID NOs:76-98, described by Janssen et al. in U.S. Patent Application Publication No. 2003/0152976 and by Janssen et al. in WO 04048399, respectively. For bleached hair, the fingernail-binding peptide, given as SEQ ID NO:60, may also be used.

Coloring agents as herein defined are any dye, pigment, and the like that may be used to change the color of hair, skin, or nails. In the peptide-based hair colorants of the present invention, any known coloring agent may be used. Hair coloring agents are well known in the art (see for example Green et al. supra, *CFTA International Color Handbook*, $2^{nd}$ ed., Micelle Press, England (1992) and *Cosmetic Handbook*, US Food and Drug Administration, FDA/IAS Booklet (1992)), and are available commercially from various sources (for example Bayer, Pittsburgh, Pa.; Ciba-Geigy, Tarrytown, N.Y.; ICI, Bridgewater, N.J.; Sandoz, Vienna, Austria; BASF, Mount Olive, N.J.; and Hoechst, Frankfurt, Germany). Suitable hair coloring agents include, but are not limited to dyes, such as 4-hydroxypropylamino-3-nitrophenol, 4-amino-3-nitrophenol, 2-amino-6-chloro-4-nitrophenol, 2-nitro-par-aphenylenediamine, N,N-hydroxyethyl-2-nitro-phenylene-diamine, 4-nitro-indole, Henna, HC Blue 1, HC Blue 2, HC Yellow 4, HC Red 3, HC Red 5, Disperse Violet 4, Disperse Black 9, HC Blue 7, HC Blue 12, HC Yellow 2, HC Yellow 6, HC Yellow 8, HC Yellow 12, HC Brown 2, D&C Yellow 1, D&C Yellow 3, D&C Blue 1, Disperse Blue 3, Disperse violet 1, eosin derivatives such as D&C Red No. 21 and halogenated fluorescein derivatives such as D&C Red No. 27, D&C Red Orange No. 5 in combination with D&C Red No. 21 and D&C Orange No. 10; and pigments, such as D&C Red No. 36 and D&C Orange No. 17, the calcium lakes of D&C Red Nos. 7, 11, 31 and 34, the barium lake of D&C Red No. 12, the strontium lake of D&C Red No. 13, the aluminum lakes of FD&C Yellow No. 5, of FD&C Yellow No. 6, of D&C Red No. 27, of D&C Red No. 21, and of FD&C Blue No. 1, iron oxides, manganese violet, chromium oxide, titanium dioxide, zinc oxide, barium oxide, ultramarine blue, bismuth citrate, and carbon black particles. The preferred hair coloring agents of the present invention are D&C Yellow 1 and 3, HC Yellow 6 and 8, D&C Blue 1, HC Blue 1, HC Brown 2, HC Red 5,2-nitro-paraphenylenediamine, N,N-hydroxyethyl-2-nitro-phenylenediamine, 4-nitro-indole, and carbon black.

Metallic and semiconductor nanoparticles may also be used as hair coloring agents due to their strong emission of light (Vic et al. U.S. Patent Application Publication No. 2004/0010864). "Nanoparticles" are herein defined as metallic or semiconductor particles with an average particle diameter of between 1 and 100 nm. Preferably, the average particle diameter of the particles is between about 1 and 40 nm. As used herein, "particle size" and "particle diameter" have the same meaning. The metallic nanoparticles include, but are not limited to, particles of gold, silver, platinum, palladium, iridium, rhodium, osmium, iron, copper, cobalt, and alloys composed of these metals. An "alloy" is herein defined as a homogeneous mixture of two or more metals. The "semiconductor nanoparticles" include, but are not limited to, particles of cadmium selenide, cadmium sulfide, silver sulfide, cadmium sulfide, zinc oxide, zinc sulfide, zinc selenide, lead sulfide, gallium arsenide, silicon, tin oxide, iron oxide, and indium phosphide. The nanoparticles are stabilized and made water-soluble by the use of a suitable organic coating or monolayer. As used herein, monolayer-protected nanoparticles are one type of stabilized nanoparticle. Methods for the preparation of stabilized, water-soluble metal and semiconductor nano-particles are known in the art, and are described by Huang et al. in copending U.S. patent application Ser. No. 10/622,889, which is incorporated herein by reference. The color of the nanoparticles depends on the size of the particles. Therefore, by controlling the size of the nanoparticles, different colors may be obtained. For example, ZnS-coated CdSe nanoparticles cover the entire visible spectrum over a particle size range of 2 to 6 nm. Specifically, CdSe nanoparticles with a core size of 2.3, 4.2, 4.8 and 5.5 nm emit light at the wavelength centered around 485, 565, 590, and 625 nm, respectively. Water-soluble nanoparticles of different sizes may be obtained from a broad size distribution of nanoparticles using the size fractionation method described by Huang, supra. That method comprises the regulated addition of a water-miscible organic solvent to a solution of nanoparticles in the presence of an electrolyte. Increasing additions of the water-miscible organic solvent result in the precipitation of nanoparticles of decreasing size.

The peptide-based hair colorants of the present invention are prepared by covalently attaching a specific hair-binding peptide to a coloring agent, either directly or via a spacer. Any of the coupling methods described above may be used. It may be necessary to introduce reactive groups, such as carboxylic acid, alcohol, amine, or aldehyde groups, on the coloring agent for coupling to the hair-binding peptide. These modifications may be done using routine chemistry, which is well known in the art. For example, the surface of carbon black particles may be oxidized using nitric acid, a peroxide such as hydrogen peroxide, or an inorganic initiator such as ammonium persulfate, to generate functional groups. Preferably, the carbon black surface is oxidized using ammonium persulfate as described by Carrasco-Marin et al. (*J. Chem. Soc., Faraday Trans.* 93:2211-2215 (1997)). Amino functional groups may be introduced to the surface of carbon black using an organic initiator such as 2,2'-Azobis(2-methylpropiona-mide)-dihydrochloride. The inorganic pigments and the nanoparticles may be derivatized to introduce carboxylic acid or amino functional groups in a similar manner.

It may also be desirable to have multiple hair-binding peptides attached to the coloring agent to enhance the interaction between the peptide-based hair colorant and the hair. Either multiple copies of the same hair-binding peptide or a combination of different hair-binding peptides may be used. In the case of large pigment particles, a large number of hair-binding peptides, i.e., up to about 10,000, may be attached to the pigment. A smaller number of hair-binding peptides can be attached to the smaller dye molecules, i.e., up to about 50. Therefore, in one embodiment of the present invention, the peptide-based hair colorants are diblock compositions consisting of a hair-binding peptide (HBP) and a coloring agent (C), having the general structure $(HBP)_n$-C, where n ranges from 1 to about 10,000, preferably n is 1 to about 500.

In another embodiment, the peptide-based hair colorants contain a spacer (S) separating the binding peptide from the hair coloring agent, as described above. Multiple copies of the hair-binding peptide may be attached to a single spacer molecule. In this embodiment, the peptide-based hair colorants are triblock compositions consisting of a hair-binding peptide, a spacer, and a coloring agent, having the general structure $[(HBP)_m-S]_n$-C, where n ranges from 1 to about 10,000, preferably n is 1 to about 500, and m ranges from 1 to about 50, preferably m is 1 to about 10.

The peptide-based hair colorants of the present invention may be used in hair coloring compositions for dyeing hair. Hair coloring compositions are herein defined as compositions for the coloring, dyeing, or bleaching of hair, comprising an effective amount of peptide-based hair colorant or a mixture of different peptide-based hair colorants in a cosmetically acceptable medium. An effective amount of a peptide-based hair colorant for use in a hair coloring composition is herein defined as a proportion of from about 0.001% to about 20% by weight relative to the total weight of the composition. Components of a cosmetically acceptable medium for hair coloring compositions are described by Dias et al., in U.S. Pat. No. 6,398,821 and by Deutz et al., in U.S. Pat. No. 6,129,770, both of which are incorporated herein by reference. For example, hair coloring compositions may contain sequestrants, stabilizers, thickeners, buffers, carriers, surfactants, solvents, antioxidants, polymers, and conditioners. The conditioners may include the peptide-based hair conditioners and hair-binding peptides of the present invention in a proportion from about 0.01% to about 10%, preferably about 0.01% to about 5% by weight relative to the total weight of the hair coloring composition.

The peptide-based hair colorants of the present invention may also be used as coloring agents in cosmetic compositions that are applied to the eyelashes or eyebrows including, but not limited to, mascaras, and eyebrow pencils. These may be anhydrous make-up products comprising a cosmetically acceptable medium which contains a fatty substance in a proportion generally of from about 10 to about 90% by weight relative to the total weight of the composition, where the fatty phase containing at least one liquid, solid or semi-solid fatty substance, as described above. The fatty substance includes, but is not limited to, oils, waxes, gums, and so-called pasty fatty substances. Alternatively, these compositions may be in the form of a stable dispersion such as a water-in-oil or oil-in-water emulsion, as described above. In these compositions, the proportion of the peptide-based hair colorant is generally from about 0.001% to about 20% by weight relative to the total weight of the composition.

Peptide-Based Nail Colorants

The peptide-based nail colorants of the present invention are formed by coupling a nail-binding peptide (NBP) with a coloring agent (C). The nail-binding peptide part of the peptide-based nail colorant binds strongly to the fingernails or toenails, thus keeping the coloring agent attached to the nails for a long lasting coloring effect. The nail-binding peptides include, but are not limited to nail-binding peptides selected by the screening methods described above, including the nail-binding peptide sequences of the invention, given by SEQ ID NOs:53 and 60, most preferably the peptide given by SEQ ID NO:60. Additionally, the beached hair-binding peptides, given as SEQ ID NOs:7, 8, 19-27 38, 39, 40, 43-45, 47, 57, 58. and 59 may be used.

The peptide-based nail colorants of the present invention are prepared by covalently attaching a specific nail-binding peptide to a coloring agent, either directly or via a spacer, using any of the coupling methods described above. In the peptide-based nail colorants of the present invention, any of the coloring agents described above may be used. The preferred coloring agents for use in the peptide-based nail colorants of the present invention include D&C Red Nos. 8, 10, 30 and 36, the barium lakes of D&C Red Nos. 6, 9 and 12, the calcium lakes of D&C Red Nos. 7, 11, 31 and 34, the strontium lake of D&C Red No. 30 and D&C Orange No. 17 and D&C Blue No. 6.

It may also be desirable to have multiple nail-binding peptides attached to the coloring agent to enhance the interaction between the peptide-based nail colorant and the nails. Either multiple copies of the same nail-binding peptide or a combination of different nail-binding peptides may be used. In the case of large pigment particles, a large number of nail-binding peptides, i.e., up to about 10,000, may be attached to the pigment. A smaller number of nail-binding peptides can be attached to the smaller dye molecules, i.e., up to about 50. Therefore, in one embodiment of the present invention, the peptide-based nail colorants are diblock compositions consisting of a nail-binding peptide (NBP) and a coloring agent (C), having the general structure $(NBP)_n$-C, where n ranges from 1 to about 10,000, preferably n is 1 to about 500.

In another embodiment, the peptide-based nail colorants contain a spacer (S) separating the binding peptide from the coloring agent, as described above. Multiple copies of the nail-binding peptide may be attached to a single spacer molecule. In this embodiment, the peptide-based nail colorants are triblock compositions consisting of a nail-binding peptide, a spacer, and a coloring agent, having the general structure $[(NBP)_m-S]_n$-C, where n ranges from 1 to about 10,000, preferably n is 1 to about 500, and m ranges from 1 to about 50, preferably m is 1 to about 10.

The peptide-based nail colorants of the present invention may be used in nail polish compositions for coloring fingernails and toenails. Nail polish compositions are herein defined as compositions for the treatment and coloring of nails, comprising an effective amount of a peptide-based nail colorant or a mixture of different peptide-based nail colorants in a cosmetically acceptable medium. An effective amount of a peptide-based nail colorant for use in a nail polish composition is herein defined as a proportion of from about 0.001% to about 20% by weight relative to the total weight of the composition. Components of a cosmetically acceptable medium for nail polishes are described by Philippe et al. supra. The nail polish composition typically contains a solvent and a film forming substance, such as cellulose derivatives, polyvinyl derivatives, acrylic polymers or copolymers, vinyl copolymers and polyester polymers. Additionally, the nail polish may contain a plasticizer, such as tricresyl phosphate, benzyl benzoate, tributyl phosphate, butyl acetyl ricinoleate, triethyl citrate, tributyl acetyl citrate, dibutyl phthalate or camphor.

Peptide-Based Skin Colorants

The peptide-based skin colorants of the present invention are formed by coupling a skin-binding peptide (SBP) with a coloring agent (C). The skin-binding peptide part of the peptide-based skin colorant binds strongly to the skin, thus keeping the coloring agent attached to the skin for a long lasting skin coloring effect. The skin-binding peptides include, but are not limited to, skin-binding peptides selected by the screening methods described above, including the skin-binding peptide sequence of the invention, given as SEQ ID NOs: 61. Additionally, any known skin-binding peptide may be used, including but not limited to SEQ ID NO:2, and SEQ ID NOs:99-104, described by Janssen et al. in U.S. Patent Application Publication No. 2003/0152976 and by Janssen et al. in WO 04048399, respectively.

The peptide-based skin colorants of the present invention are prepared by covalently attaching a specific skin-binding peptide to a coloring agent, either directly or via a spacer, using any of the coupling methods described above. Any of the colorants described above may be used. The preferred coloring agents for use in the peptide-based skin colorants of the present invention include the following dyes: eosin derivatives such as D&C Red No. 21 and halogenated fluorescein derivatives such as D&C Red No. 27, D&C Red Orange No. 5 in combination with D&C Red No. 21 and D&C Orange No. 10, and the pigments: titanium dioxide, zinc oxide, D&C Red No. 36 and D&C Orange No. 17, the calcium lakes of D&C Red Nos. 7, 11, 31 and 34, the barium lake of D&C Red No. 12, the strontium lake D&C Red No. 13, the aluminum lakes of FD&C Yellow No. 5, of FD&C Yellow No. 6, of D&C Red No. 27, of D&C Red No. 21, of FD&C Blue No. 1, iron oxides, manganese violet, chromium oxide, ultramarine blue, and carbon black. The coloring agent may also be a sunless tanning agent, such as dihydroxyacetone, that produces a tanned appearance on the skin without exposure to the sun.

It may also be desirable to have multiple skin-binding peptides attached to the coloring agent to enhance the interaction between the peptide-based skin colorant and the skin. Either multiple copies of the same skin-binding peptide or a combination of different skin-binding peptides may be used. In the case of large pigment particles, a large number of skin-binding peptides, i.e., up to about 10,000, may be attached to the pigment. A smaller number of skin-binding peptides can be attached to the smaller dye molecules, i.e., up to about 50. Therefore, in one embodiment of the present invention, the peptide-based skin colorants are diblock compositions consisting of a skin-binding peptide (SBP) and a coloring agent (C), having the general structure $(SBP)_n$-C, where n ranges from 1 to about 10,000, preferably n is 1 to about 500.

In another embodiment, the peptide-based skin colorants contain a spacer (S) separating the binding peptide from the coloring agent, as described above. Multiple copies of the skin-binding peptide may be attached to a single spacer molecule. In this embodiment, the peptide-based skin colorants are triblock compositions consisting of a skin-binding peptide, a spacer, and a coloring agent, having the general structure $[(SBP)_m-S]_n$-C, where n ranges from 1 to about 10,000, preferably n is 1 to about 500, and m ranges from 1 to about 50, preferably m is 1 to about 10.

The peptide-based skin colorants of the present invention may be used as coloring agents in cosmetic and make-up products, including but not limited to foundations, blushes, lipsticks, lip liners, lip glosses, eyeshadows and eyeliners. These may be anhydrous make-up products comprising a cosmetically acceptable medium which contains a fatty substance, or they may be in the form of a stable dispersion such as a water-in-oil or oil-in-water emulsion, as described above. In these compositions, the proportion of the peptide-based skin colorant is generally from about 0.001% to about 40% by weight relative to the total weight of the composition.

Methods for Treating Hair, Skin, and Nails

In another embodiment, methods are provided for treating hair, skin, and nails, with the peptide-based conditioners and colorants of the present invention. Specifically, the present invention also comprises a method for forming a protective film of peptide-based conditioner on skin, hair, or lips by applying one of the compositions described above comprising an effective amount of a peptide-based skin conditioner or peptide-based hair conditioner to the skin, hair, or lips and allowing the formation of the protective film. The compositions of the present invention may be applied to the skin, hair, or lips by various means, including, but not limited to spraying, brushing, and applying by hand. The peptide-based conditioner composition is left in contact with the skin, hair, or lips for a period of time sufficient to form the protective film, preferably for at least about 0.1 to 60 min.

The present invention also provides a method for coloring hair by applying a hair coloring composition comprising an effective amount of a peptide-based hair colorant to the hair by means described above. The hair coloring composition is allowed to contact the hair for a period of time sufficient to cause coloration of the hair, preferably between about 5 to about 50 min, and then the hair coloring composition may be rinsed from the hair.

The present invention also provides a method for coloring skin or lips by applying a skin coloring composition comprising an effective amount of a peptide-based skin colorant to the skin or lips by means described above.

The present invention also provides a method for coloring fingernails or toenails by applying a nail polish composition comprising an effective amount of a peptide-based nail colorant to the fingernails or toenails by means described above.

The present invention also provides a method for coloring eyebrows and eyelashes by applying a cosmetic composition comprising an effective amount of a peptide-based hair colorant to the eyebrows and eyelashes by means described above.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "sec" means second(s), "h" means hour(s), "μL" means microliter(s), "mL" means milliliter(s), "L" means liter(s), "nm" means nanometer(s), "mm" means millimeter(s), "cm" means centimeter(s), "μm" means micrometer(s), "mM" means millimolar, "M" means molar, "mmol" means millimole(s), "pmole" means micromole(s), "g" means gram(s), "μg" means microgram(s), "mg" means milligram(s), "g" means the gravitation constant, "rpm" means revolutions per minute, "pfu" means plague forming unit, "BSA" means bovine serum albumin, "ELISA" means enzyme linked immunosorbent assay, "IPTG" means isopropyl β-D-thiogalactopyranoside, "A" means absorbance, "$A_{450}$" means the absorbance measured at a wavelength of 450 nm, "TBS" means Tris-buffered saline, "TBST-X" means Tris-buffered saline containing Tween® 20 where "X" is the weight percent of Tween® 20, "Xgal" means 5-bromo-4-chloro-3-indolyl-beta-D-galactopyranoside, "SEM" means standard error of the mean, "ESCA" means electron spectroscopy for chemical analysis, "eV" means electron volt(s), "TGA" means thermogravimetric analysis, "GPC" means gel permeation chromatography, "MW" means molecular weight, "$M_w$" means weight-average molecular weight, "vol %" means volume percent.

General Methods:

Standard recombinant DNA and molecular cloning techniques used in the Examples are well known in the art and are described by Sambrook, J., Fritsch, E. F. and Maniatis, T., *Molecular Cloning: A Laboratory Manual*, Cold Spring Harbor Laboratory Press, Cold Spring Harbor, N.Y., 1989, by T. J. Silhavy, M. L. Bennan, and L. W. Enquist, *Experiments with Gene Fusions*, Cold Spring Harbor Laboratory, Cold Spring Harbor, N.Y., 1984, and by Ausubel, F. M. et al., *Current Protocols in Molecular Biology*, Greene Publishing Assoc. and Wiley-Interscience, N.Y., 1987.

Materials and methods suitable for the maintenance and growth of bacterial cultures are also well known in the art. Techniques suitable for use in the following Examples may be found in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, D.C., 1994, or by Thomas D. Brock in *Biotechnology: A Textbook of Industrial Microbiology*, Second Edition, Sinauer Associates, Inc., Sunderland, Mass., 1989. All reagents, restriction enzymes and materials used for the growth and maintenance of bacterial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.), unless otherwise specified.

Example 1

Selection of Hair-Binding Phage Peptides Using Standard Biopanning

The purpose of this Example was to identify hair-binding phage peptides that bind to normal hair and to bleached hair using standard phage display biopanning.

Phage Display Peptide Libraries:

The phage libraries used in the present invention, Ph.D.-12™ Phage Display Peptide Library Kit and Ph.D.-7™ Phage Display Library Kit, were purchased from New England BioLabs (Beverly, Mass.). These kits are based on a combinatorial library of random peptide 7 or 12-mers fused to a minor coat protein (pIII) of M13 phage. The displayed peptide is expressed at the N-terminus of pIII, such that after the signal peptide is cleaved, the first residue of the coat protein is the first residue of the displayed peptide. The Ph.D.-7 and Ph.D.-12 libraries consist of approximately $2.8 \times 10^9$ and $2.7 \times 10^9$ sequences, respectively. A volume of 10 μL contains about 55 copies of each peptide sequence. Each initial round of experiments was carried out using the original library provided by the manufacture in order to avoid introducing any bias into the results.

Preparation of Hair Samples:

The samples used as normal hair were 6-inch medium brown human hairs obtained from International Hair Importers and Products (Bellerose, N.Y.). The hairs were placed in 90% isopropanol for 30 min at room temperature and then washed 5 times for 10 min each with deionized water. The hairs were air-dried overnight at room temperature.

To prepare the bleached hair samples, the medium brown human hairs were placed in 6% $H_2O_2$, which was adjusted to pH 10.2 with ammonium hydroxide, for 10 min at room temperature and then washed 5 times for 10 min each with deionized water. The hairs were air-dried overnight at room temperature.

The normal and bleached hair samples were cut into 0.5 to 1 cm lengths and about 5 to 10 mg of the hairs was placed into wells of a custom 24-well biopanning apparatus that had a pig skin bottom. An equal number of the pig skin bottom wells were left empty. The pig skin bottom apparatus was used as a subtractive procedure to remove phage-peptides that have an affinity for skin. This apparatus was created by modifying a dot blot apparatus (obtained from Schleicher & Schuell, Keene, N.H.) to fit the biopanning process. Specifically, the top 96-well block of the dot blot apparatus was replaced by a 24-well block. A 4×6 inch treated pig skin was placed under the 24-well block and panning wells with a pig skin bottom were formed by tightening the apparatus. The pig skin was purchased from a local supermarket and stored at −80° C. Before use, the skin was placed in deionized water to thaw, and then blotted dry using a paper towel. The surface of the skin was wiped with 90% isopropanol, and then rinsed with deionized water. The 24-well apparatus was filled with blocking buffer consisting of 1 mg/mL BSA in TBST containing 0.5% Tween® 20 (TBST-0.5%) and incubated for 1 h at 4° C. The wells and hairs were washed 5 times with TBST-0.5%. One milliliter of TBST-0.5% containing 1 mg/mL BSA was added to each well. Then, 10 µL of the original phage library ($2 \times 10^{11}$ pfu), either the 12-mer or 7-mer library, was added to the pig skin bottom wells that did not contain a hair sample and the phage library was incubated for 15 min at room temperature. The unbound phages were then transferred to pig skin bottom wells containing the hair samples and were incubated for 15 min at room temperature. The hair samples and the wells were washed 10 times with TBST-0.5%. The hairs were then transferred to clean, plastic bottom wells of a 24-well plate and 1 mL of a non-specific elution buffer consisting of 1 mg/mL BSA in 0.2 M glycine-HCl, pH 2.2, was added to each well and incubated for 10 min to elute the bound phages. Then, 160 µL of neutralization buffer consisting of 1 M Tris-HCl, pH 9.2, was added to each well. The eluted phages from each well were transferred to a new tube for titering and sequencing.

To titer the bound phages, the eluted phage was diluted with SM buffer (100 mM NaCl, 12.3 mM $MgSO_4.7H_2O$, 50 mM Tris-HCl, pH 7.5, and 0.01 wt/vol % gelatin) to prepare 10-fold serial dilutions of $10^1$ to $10^4$. A 10 µL aliquot of each dilution was incubated with 200 µL of mid-log phase *E. coli* ER2738 (New England BioLabs), grown in LB medium for 20 min and then mixed with 3 mL of agarose top (LB medium with 5 mM $MgCl_2$, and 0.7% agarose) at 45° C. This mixture was spread onto a S-Gal™/LB agar plate (Sigma Chemical Co.) and incubated overnight at 37° C. The S-Gal™/LB agar blend contained 5 g of tryptone, 2.5 g of yeast extract, 5 g of sodium chloride, 6 g of agar, 150 mg of 3,4-cyclohexenoesculetin-β-D-galactopyranoside (S-Gal™), 250 mg of ferric ammonium citrate and 15 mg of isopropyl β-D-thiogalactoside (IPTG) in 500 mL of distilled water. The plates were prepared by autoclaving the S-Gal™/LB for 15 to 20 min at 121-124° C. The single black plaques were randomly picked for DNA isolation and sequence analysis.

The remaining eluted phages were amplified by incubating with diluted *E. coli* ER2738, from an overnight culture diluted 1:100 in LB medium, at 37° C. for 4.5 h. After this time, the cell culture was centrifuged for 30 s and the upper 80% of the supernatant was transferred to a fresh tube, ⅙ volume of PEG/NaCl (20% polyethylene glyco-800, 2.5 M sodium chloride) was added, and the phage was allowed to precipitate overnight at 4° C. The precipitate was collected by centrifugation at 10,000×g at 4° C. and the resulting pellet was resuspended in 1 mL of TBS. This was the first round of amplified stock. The amplified first round phage stock was then titered according to the same method as described above. For the next round of biopanning, more than $2 \times 10^{11}$ pfu of phage stock from the first round was used. The biopanning process was repeated for 3 to 6 rounds depending on the experiments.

The single plaque lysates were prepared following the manufacture's instructions (New England Labs) and the single stranded phage genomic DNA was purified using the QIAprep Spin M13 Kit (Qiagen, Valencia, Calif.) and sequenced at the DuPont Sequencing Facility using—96 gIII sequencing primer (5'-CCCTCATAGTTAGCGTMCG-3'), given as SEQ ID NO:62. The displayed peptide is located immediately after the signal peptide of gene III.

The amino acid sequences of the eluted normal hair-binding phage peptides from the 12-mer library isolated from the fifth round of biopanning are given in Table 1. The amino acid sequences of the eluted bleached hair-binding phage peptides from the 12-mer library isolated from the fifth round of biopanning are given in Table 2. Repeated amino acid sequences of the eluted normal hair-binding phage peptides from the 7-mer library from 95 randomly selected clones, isolated from the third round of biopanning, are given in Table 3.

TABLE 1

Amino Acid Sequences of Eluted Normal Hair-Binding Phage Peptides from 12-Mer Library

| Clone ID | Amino Acid Sequence | SEQ ID NO: | Frequency[1] |
|---|---|---|---|
| 1 | RVPNKTVTVDGA | 5 | 5 |
| 2 | DRHKSKYSSTKS | 6 | 2 |
| 3 | KNFPQQKEFPLS | 7 | 2 |
| 4 | QRNSPPAMSRRD | 8 | 2 |
| 5 | TRKPNMPHGQYL | 9 | 2 |
| 6 | KPPHLAKLPFTT | 10 | 1 |
| 7 | NKRPPTSHRIHA | 11 | 1 |
| 8 | NLPRYQPPCKPL | 12 | 1 |
| 9 | RPPWKKPIPPSE | 13 | 1 |
| 10 | RQRPKDHFFSRP | 14 | 1 |

TABLE 1-continued

Amino Acid Sequences of Eluted Normal Hair-Binding Phage Peptides from 12-Mer Library

| Clone ID | Amino Acid Sequence | SEQ ID NO: | Frequency[1] |
|---|---|---|---|
| 11 | SVPNKXVTVDGX | 15 | 1 |
| 12 | TTKWRHRAPVSP | 16 | 1 |
| 13 | WLGKNRIKPRAS | 17 | 1 |
| 14 | SNFKTPLPLTQS | 18 | 1 |
| 15 | SVSVGMKPSPRP | 3 | 1 |

[1] The frequency represents the number of identical sequences that occurred out of 23 sequenced clones.

TABLE 2

Amino Acid Sequences of Eluted Bleached Hair-Binding Phage Peptides from 12-Mer Library

| Clone ID | Amino Acid Sequence | SEQ ID NO: | Frequency[1] |
|---|---|---|---|
| 1 | KELQTRNVVQRE | 19 | 8 |
| 2 | QRNSPPAMSRRD | 8 | 5 |
| 3 | TPTANQFTQSVP | 20 | 2 |
| 4 | AAGLSQKHERNR | 21 | 2 |
| 5 | ETVHQTPLSDRP | 22 | 1 |
| 6 | KNFPQQKEFPLS | 7 | 1 |
| 7 | LPALHIQRHPRM | 23 | 1 |
| 8 | QPSHSQSHNLRS | 24 | 1 |
| 9 | RGSQKSKPPRPP | 25 | 1 |
| 10 | THTQKTPLLYYH | 26 | 1 |
| 11 | TKGSSQAILKST | 27 | 1 |

[1] The frequency represents the number of identical sequences that occurred out of 24 sequenced clones.

TABLE 3

Amino Acid Sequences of Eluted Normal Hair-Binding Phage Peptides from 7-Mer Library

| Clone ID | Amino Acid Sequence | SEQ ID NO: |
|---|---|---|
| A | DLHTVYH | 28 |
| B | HIKPPTR | 29 |
| D | HPVWPAI | 30 |
| E | MPLYYLQ | 31 |
| F[1] | HLTVPWRGGGSAVPFYSHSQITLPNHGPHD | 32 |
| G[1] | TSSGGVRPNLHHTSKKEKRENRKVPFYSHS | 33 |
| | VTSRGNV | |
| H | KHPTYRQ | 34 |
| I | HPMSAPR | 35 |
| J | MPKYYLQ | 36 |

[1] There was a multiple DNA fragment intersion in these clones.

Example 2

Selection of High Affinity Hair-Binding Phage Peptides Using a Modified Method

The purpose of this Example was to identify hair-binding phage peptides with a higher binding affinity.

The hairs that were treated with the acidic elution buffer, as described in Example 1, were washed three more times with the elution buffer and then washed three times with TBST-0.5%. These hairs, which had acid resistant phage peptides still attached, were used to directly infect 500 μL of mid-log phase bacterial host cells, E. coli ER2738 (New England BioLabs), which were then grown in LB medium for 20 min and then mixed with 3 mL of agarose top (LB medium with 5 mM $MgCl_2$, and 0.7% agarose) at 45° C. This mixture was spread onto a LB medium/IPTG/S-Gal™ plate (LB medium with 15 g/L agar, 0.05 g/L IPTG, and 0.04 g/L S-Gal™) and incubated overnight at 37° C. The black plaques were counted to calculate the phage titer. The single black plaques were randomly picked for DNA isolation and sequencing analysis, as described in Example 1. This process was performed on the normal and bleached hair samples that were screened with the 7-mer and 12-mer phage display libraries, as described in Example 1. The amino acid sequences of these high affinity, hair-binding phage peptides are given in Tables 4-7.

TABLE 4

Amino Acid Sequences of High Affinity, Normal Hair-Binding Phage Peptides from 7-Mer Library

| Clone ID | Amino Acid Sequence | SEQ ID NO: |
|---|---|---|
| D5 | GPHDTSSGGVRPNLHHTSKKEKRENRKVPFYSHSVTSRGNV[1] | 33 |
| A36 | MHAHSIA | 37 |
| B41 | TAATTSP | 38 |

[1] There was a multiple DNA fragment intersion in this clone.

TABLE 5

Amino Acid Sequences of High Affinity, Bleached Hair-Binding Phage Peptides from 7-Mer Library

| Clone ID | Amino Acid Sequence | SEQ ID NO: |
|---|---|---|
| D39 | LGIPQNL | 39 |
| B1 | TAATTSP | 38 |

TABLE 6

Amino Acid Sequences of High Affinity, Normal Hair-Binding Phage Peptides from 12-Mer Library

| Clone ID | Amino Acid Sequence | SEQ ID NO: |
|---|---|---|
| C2 | AKPISQHLQRGS | 40 |
| A3 | APPTPAAASATT | 41 |
| F9 | DPTEGARRTIMT | 42 |
| A19 | EQISGSLVAAPW | 43 |
| F4 | LDTSFPPVPFHA | 44 |
| F35 | LPRIANTWSPS | 45 |
| D21 | RTNAADHPAAVT | 46 |
| C10 | SLNWVTIPGPKI | 47 |
| C5 | TDMQAPTKSYSN | 48 |
| D20 | TIMTKSPSLSCG | 49 |
| C18 | TPALDGLRQPLR | 50 |
| A20 | TYPASRLPLLAP | 51 |
| C13 | AKTHKHPAPSYS | 52 |
| G-D20 | YPSFSPTYRPAF | 53 |
| A23 | TDPTPFSISPER | 54 |
| F67 | SQNWQDSTSYSN | 55 |
| F91 | WHDKPQNSSKST | 56 |
| G-F1 | LDVESYKGTSMP | 4 |

TABLE 7

Amino Acid Sequences of High Affinity, Bleached Hair-Binding Phage Peptides from 12-Mer Library

| Clone ID | Amino Acid Sequence | SEQ ID NO: |
|---|---|---|
| A5 | EQISGSLVAAPW | 43 |
| C4 | NEVPARNAPWLV | 57 |
| D30 | NSPGYQADSVAIG | 58 |
| C44 | AKPISQHLQRGS | 40 |
| E66 | LDTSFPPVPFHA | 44 |
| C45 | SLNWVTIPGPKI | 47 |

TABLE 7-continued

Amino Acid Sequences of High Affinity, Bleached Hair-Binding Phage Peptides from 12-Mer Library

| Clone ID | Amino Acid Sequence | SEQ ID NO: |
|---|---|---|
| E18 | TQDSAQKSPSPL | 59 |

Example 3

Selection of High Affinity Fingernail-Binding Phage Peptides

The purpose of this Example was to identify phage peptides that have a high binding affinity to fingernails. The modified biopanning method described in Example 2 was used to identify high affinity, fingernail-binding phage-peptide clones.

Human fingernails were collected from test subjects. The fingernails were cleaned by brushing with soap solution, rinsed with deionized water, and allowed to air-dry at room temperature. The fingernails were then powdered under liquid $N_2$, and 10 mg of the fingernails was added to each well of a 96-well filter plate. The fingernail samples were treated for 1 h with blocking buffer consisting of 1 mg/mL BSA in TBST-0.5%, and then washed with TBST-0.5%. The fingernail samples were incubated with phage library (Ph.D-12 Phage Display Peptide Library Kit), and washed 10 times using the same conditions described in Example 1. After the acidic elution step, described in Example 1, the fingernail samples were washed three more times with the elution buffer and then washed three times with TBST-0.5%. The acid-treated fingernails, which had acid resistant phage peptides still attached, were used to directly infect *E. coli* ER2738 cells as described in Example 2. This biopanning process was repeated three times. A total of 75 single black phage plaques were picked randomly for DNA isolation and sequencing analysis and two repeated clones were identified. The amino acid sequences of these phage peptides are listed in Table 8. These fingernail binding peptides were also found to bind well to bleached hair.

TABLE 8

Amino Acid Sequences of High Affinity Fingernail-Binding Phage Peptides

| Clone ID | Amino Acid Sequence | SEQ ID NO: | Frequency[1] |
|---|---|---|---|
| F01 | ALPRIANTWSPS | 60 | 15 |
| D05 | YPSFSPTYRPAF | 53 | 26 |

[1]The frequency represents the number of identical sequences that occurred out of 75 sequenced clones.

Example 4

Selection of High Affinity Skin-Binding Phage Peptides

The purpose of this Example was to identify phage peptides that have a high binding affinity to skin. The modified biopanning method described in Examples 2 and 4 was used to identify the high affinity, skin-binding phage-peptide clones. Pig skin served as a model for human skin in the process.

The pig skin was prepared as described in Example 1. Three rounds of screenings were performed with the custom, pig skin bottom biopanning apparatus using the same procedure described in Example 4. A total of 28 single black phage plaques were picked randomly for DNA isolation and sequencing analysis and one repeated clone was identified. The amino acid sequence of this phage peptide, which appeared 9 times out of the 28 sequences, was TPFH-SPENAPGS, given as SEQ ID NO:61.

Example 5

Quantitative Characterization of the Binding Affinity of Hair-Binding Phage Clones The purpose of this Example was to quantify the binding affinity of phage clones by titering and ELISA.

Titering of Hair-Binding Phage Clones:

Phage clones displaying specific peptides were used for comparing the binding characteristics of different peptide sequences. A titer-based assay was used to quantify the phage binding. This assay measures the output pfu retained by 10 mg of hair surfaces, having a signal to noise ratio of $10^3$ to $10^4$. The input for all the phage clones was $10^{14}$ pfu. It should be emphasized that this assay measures the peptide-expressing phage particle, rather than peptide binding.

Normal hairs were cut into 0.5 cm lengths and 10 mg of the cut hair was placed in each well of a 96-well filter plate (Qiagen). Then, the wells were filled with blocking buffer containing 1 mg/mL BSA in TBST-0.5% and incubated for 1 h at 4° C. The hairs were washed 5 times with TBST-0.5%. The wells were then filled with 1 mL of TBST-0.5% containing 1 mg/mL BSA and then purified phage clones ($10^{14}$ pfu) were added to each well. The hair samples were incubated for 15 min at room temperature and then washed 10 times with TBST-0.5%. The hairs were transferred to a clean well and 1.0 mL of a non-specific elution buffer, consisting of 1 mg/mL BSA in 0.2 M Glycine-HCl at pH 2.2, was added to each well. The samples were incubated for 10 min and then 160 µL of neutralization buffer (1 M Tris-HCl, pH 9.2) was added to each well. The eluted phages from each well were transferred to a new tube for titering and sequencing analysis.

To titer the bound phages, the eluted phage was diluted with SM buffer to prepare 10-fold serial dilutions of $10^1$ to $10^8$. A 10 µL aliquot of each dilution was incubated with 200 µL of mid-log phase E. coli ER2738 (New England BioLabs), and grown in LB medium for 20 min and then mixed with 3 mL of agarose top (LB medium with 5 mM $MgCl_2$, and 0.7% agarose) at 45° C. This mixture was spread onto a LB medium/IPTG/Xgal plate (LB medium with 15 g/L agar, 0.05 g/L IPTG, and 0.04 g/L Xgal) and incubated overnight at 37° C. The blue plaques were counted to calculate the phage titers, which are given in Table 9.

TABLE 9

Titer of Hair-Binding Phage Clones

| Clone ID | SEQ ID NO: | Phage Titer |
|---|---|---|
| A | 28 | $7.50 \times 10^4$ |
| B | 29 | $1.21 \times 10^5$ |
| D | 30 | $8.20 \times 10^4$ |
| E | 31 | $1.70 \times 10^5$ |
| F | 32 | $1.11 \times 10^6$ |
| G | 33 | $1.67 \times 10^8$ |
| H | 34 | $1.30 \times 10^6$ |
| I | 35 | $1.17 \times 10^6$ |
| J | 36 | $1.24 \times 10^6$ |

Characterization of Hair-Binding Phage Clones by ELISA:

Enzyme-linked immunosorbent assay (ELISA) was used to evaluate the hair-binding specificity of selected phage-peptide clones. Phage-peptide clones identified in Examples 1 and 2 along with a randomly chosen control G-F9, KHGP-DLLRSAPR (given as SEQ ID NO:63) were amplified. More than $10^{14}$ pfu phages were added to pre-blocked hair surfaces. The same amount of phages was also added to pre-blocked pig skin surfaces as a control to demonstrate the hair-binding specificity.

A unique hair or pig skin-bottom 96-well apparatus was created by applying one layer of Parafilm® under the top 96-well block of a Minifold I Dot-Blot System (Schleicher & Schuell, Inc., Keene, N.H.), adding hair or a layer of hairless pig skin on top of the Parafilm® cover, and then tightening the apparatus. For each clone to be tested, the hair-covered well was incubated for 1 h at room temperature with 200 µL of blocking buffer, consisting of 2% non-fat dry milk (Schleicher & Schuell, Inc.) in TBS. A second Minifold system with pig skin at the bottom of the wells was treated with blocking buffer simultaneously to serve as a control. The blocking buffer was removed by inverting the systems and blotting them dry with paper towels. The systems were rinsed 6 times with wash buffer consisting of TBST-0.05%. The wells were filled with 200 µL of TBST-0.5% containing 1 mg/mL BSA and then 10 µL (over $10^{12}$ copies) of purified phage stock was added to each well. The samples were incubated at 37° C. for 15 min with slow shaking. The non-binding phage was removed by washing the wells 10 to 20 times with TBST-0.5%. Then, 100 µL of horseradish peroxidase/anti-M13 antibody conjugate (Amersham USA, Piscataway, N.J.), diluted 1:500 in the blocking buffer, was added to each well and incubated for 1 h at room temperature. The conjugate solution was removed and the wells were washed 6 times with TBST-0.05%. TMB substrate (200 µL), obtained from Pierce Biotechnology (Rockford, Ill.) was added to each well and the color was allowed to develop for between 5 to 30 min, typically for 10 min, at room temperature. Then, stop solution (200 µL of 2 M $H_2SO_4$) was added to each well and the solution was transferred to a 96-well plate and the $A_{450}$ was measured using a microplate spectrophotometer (Molecular Devices, Sunnyvale, Calif.). The resulting absorbance values, reported as the mean of at least three replicates, and the standard error of the mean (SEM) are given in Table 10.

TABLE 10

Results of ELISA Assay with Skin and Hair

| Clone ID | SEQ ID NO: | Hair $A_{450}$ | SEM | Pig Skin $A_{450}$ | SEM |
|---|---|---|---|---|---|
| G-F9 (Control) | 63 | 0.074 | 0.057 | −0.137 | 0.015 |
| D21 | 46 | 1.051 | 0.16 | 0.04 | 0.021 |
| D39 | 39 | 0.685 | 0.136 | 0.086 | 0.019 |
| D5 | 33 | 0.652 | 0.222 | 0.104 | 0.023 |
| A36 | 37 | 0.585 | 0.222 | 0.173 | 0.029 |
| C5 | 48 | 0.548 | 0.263 | 0.047 | 0.037 |
| C10 | 47 | 0.542 | 0.105 | 0.032 | 0.012 |
| A5 | 43 | 0.431 | 0.107 | 0.256 | 0.022 |
| B1 | 38 | 0.42 | 0.152 | 0.127 | 0.023 |
| D30 | 58 | 0.414 | 0.119 | 0.287 | 0.045 |
| C13 | 52 | 0.375 | 0.117 | 0.024 | 0.016 |
| C18 | 50 | 0.34 | 0.197 | 0.132 | 0.023 |

As can be seen from the data in Table 10, all the hair-binding clones had a significantly higher binding affinity for hair than the control. Moreover, the hair-binding clones exhibited various degrees of selectivity for hair compared to pig skin. Clone D21 had the highest selectivity for hair, having a very strong affinity for hair and a very low affinity for pig skin.

Example 6

Confirmation of Peptide Binding Specificity and Affinity

The purpose of this Example was to test the peptide binding site specificity and affinity of the hair-binding peptide D21 using a competition ELISA. The ELISA assay only detects phage particles that remain bound to the hair surface. Therefore, if the synthetic peptide competes with the phage particle for the same binding site on hair surface, the addition of the synthetic peptide into the ELISA system will significantly reduce the ELISA results due to the peptide competition.

The synthetic hair-binding peptide D21, given as SEQ ID NO:46, was synthesized by SynPep (Dublin, Calif.). As a control, an unrelated synthetic skin-binding peptide, given as SEQ ID NO:61, was added to the system. The experimental conditions were similar to those used in the ELISA method described in Example 5. Briefly, 100 μL of Binding Buffer (1×TBS with 0.1% Tween®20 and 1 mg/mL BSA) and $10^{11}$ pfu of the pure D21 phage particles were added to each well of the 96-well filter plate, which contained a sample of normal hair. The synthetic peptide (100 μg) was added to each well (corresponding to concentration of 0.8 mM). The reactions were carried out at room temperature for 1 h with gentle shaking, followed by five washes with TBST-0.5%. The remaining steps were identical to the those used in the ELISA method described in Example 5. The ELISA results, presented as the absorbance at 450 nm ($A_{450}$), are shown in Table 11. Each individual ELISA test was performed in triplicate; the values in Table 11 are the means of the triplicate determinations.

TABLE 11

Results of Peptide Competition ELISA

| Sample | $A_{450}$ | SEM |
|---|---|---|
| Antibody-Conjugate | 0.199 | 0.031 |
| Phage D21 | 1.878 | 0.104 |
| Phage D21 and D21 Peptide | 1.022 | 0.204 |
| Phage D21 and Control Peptide | 2.141 | 0.083 |

These results demonstrated that the synthetic peptide D21 does compete with the phage clone D21 for the same binding sites on the hair surface.

Example 7

Selection of Shampoo-Resistant Hair-Binding Phage-Peptides Using Biopanning

The purpose of this Example was to select shampoo-resistant hair-binding phage-peptides using biopanning with shampoo washes.

In order to select shampoo-resistant hair-binding peptides, a biopanning experiment using 12-mer phage peptide libraries against normal and bleached hairs was performed, as described in Example 2. Instead of using normal TBST buffer to wash-off the unbounded phages, the phage-complexed hairs were washed with 10%, 30% and 50% shampoo solutions (Pantene Pro-V shampoo, Sheer Volume, Proctor & Gamble, Cincinnati, Ohio), for 5 min in separate tubes, followed by six TBS buffer washes. The washed hairs were directly used to infect host bacterial cells as described in the modified biopanning method, described in Example 2.

A potential problem with this method is the effect of the shampoo on the phage's ability to infect bacterial host cells. In a control experiment, a known amount of phage particles was added to a 10% shampoo solution for 5 min, and then a portion of the solution was used to infect bacterial cells. The titer of the shampoo-treated phage was 90% lower than that of the untreated phage. The 30% and 50% shampoo treatments gave even more severe damage to the phage's ability to infect host cells. Nevertheless, two shampoo-resistant hair-binding phage-peptides were identified, as shown in Table 12.

TABLE 12

Peptide Sequences of Shampoo-Resistant Hair-binding Phage Peptides Identified Using the Biopanning Method

| Clone | Sequence | Target | SEQ ID NO: |
|---|---|---|---|
| I-B5 | TPPELLHGDPRS | Normal and Bleached Hair | 66 |
| H-B1 | TPPTNVLMLATK | Normal Hair | 69 |

Example 8

Selection of Shampoo-Resistant Hair-Binding Phage-Peptides Using PCR

The purpose of this Example was to select shampoo-resistant hair-binding phage-peptides using a PCR method to avoid the problem of shampoo induced damage to the phage.

This principle of the PCR method is that DNA fragments inside the phage particle can be recovered using PCR, regardless of the phage's viability, and that the recovered DNA fragments, corresponding to the hair-binding peptide sequences, can then been cloned back into a phage vector and packaged into healthy phage particles.

Biopanning experiments were performed using 7-mer and 12-mer phage-peptide libraries against normal and bleached hairs, as described in Example 1. After the final wash, the phage-treated hairs were subjected to 5 min of shampoo washes, followed by six TBS buffer washes. The shampoo-washed hairs were put into a new tube filled with 1 mL of water, and boiled for 15 min to release the DNA. This DNA-containing, boiled solution was used as a DNA template for PCR reactions. The primers used in the PCR reaction were primers: M13KE-1412 Forward 5'-CAAGCCTCAGCGAC-CGAATA-3', given as SEQ ID NO:67 and M13KE-1794 Reverse 5'-CGTAACACTGAGTTTCGTCACCA-3', given SEQ ID NO:68. The PCR conditions were: 3 min denaturing at 96° C., followed by 35 cycles of 94° C. for 30 sec, 50° C. for 30 sec and 60° C. for 2 min. The PCR products (~400 bp), and M13KE vector (New England BioLabs) were digested with restriction enzymes Eag I and Acc65 I. The ligation and transformation conditions, as described in the Ph.D.™ Peptide Display Cloning System (New England Biolabs), were used. The amino acid sequence of the resulting shampoo-resistant hair-binding phage-peptide is NTSQLST, given as SEQ ID NO:70.

Example 9

Determination of the Affinity of Hair-Binding and Skin-Binding Peptides

The purpose of this Example was to determine the affinity of the hair-binding and skin-binding peptides for their respective substrates, measured as $MB_{50}$ values, using an ELISA assay.

Hair-binding and skin-binding peptides were synthesized by Synpep Inc. (Dublin, Calif.). The peptides were biotinylated by adding a biotinylated lysine residue at the C-terminus of the amino acid binding sequences for detection purposes and an amidated cysteine was added to the C-terminus of the sequence. The amino acid sequences of the peptides tested are given as SEQ ID NOs:71-74, as shown in Table 13.

For hair samples, the procedure used was as follows. The setup of the surface specific 96-well system used was the same as that described in Example 5. Briefly, the 96-wells with hair or pig skin surfaces were blocked with blocking buffer (SuperBlock™ from Pierce Chemical Co., Rockford, Ill.) at room temperature for 1 h, followed by six washes with TBST-0.5%, 2 min each, at room temperature. Various concentrations of biotinylated, binding peptide were added to each well, incubated for 15 min at 37° C., and washed six times with TBST-0.5%, 2 min each, at room temperature. Then, streptavidin-horseradish peroxidase (HRP) conjugate (Pierce Chemical Co.) was added to each well (1.0 µg per well), and incubated for 1 h at room temperature. After the incubation, the wells were washed six times with TBST-0.5%, 2 min each at room temperature. Finally, the color development and the measurement were performed as described in Example 5.

For the measurement of $MB_{50}$ of the peptide-skin complexes, the following procedure was used. First, the pigskin was treated to block the endogenous biotin in the skin. This was done by adding streptavidin to the blocking buffer. After blocking the pigskin sample, the skin was treated with D-biotin to block the excess streptavidin binding sites. The remaining steps were identical to those used for the hair samples.

The results were plotted as $A_{450}$ versus the concentration of peptide using GraphPad Prism 4.0 (GraphPad Software, Inc., San Diego, Calif.). The $MB_{50}$ values were calculated from Scatchard plots and are summarized in Table 13. The results demonstrate that the binding affinity of the hair-binding peptides (D21, F35, and I-B5) and the skin binding peptide (SEQW ID NO:61) for their respective substrate was high, while the binding affinity of the hair-binding peptides (D-21 and I-B5) for skin was relatively low.

TABLE 13

Summary of $MB_{50}$ Values for Hair and Skin-Binding Peptides

| Binding Peptide | Peptide Sequence Tested* | Substrate | $MB_{50}$, M |
|---|---|---|---|
| D21 | SEQ ID NO:71 | Normal Hair | $2 \times 10^{-6}$ |
| F35 | SEQ ID NO:72 | Bleached Hair | $3 \times 10^{-6}$ |
| I-B5 | SEQ ID NO:73 | Normal and Bleached Hair | $3 \times 10^{-7}$ |
| D21 | SEQ ID NO:71 | Pig Skin | $4 \times 10^{-5}$ |
| I-B5 | SEQ ID NO:73 | Pig Skin | $>1 \times 10^{-4}$ |
| SEQ ID NO:61 | SEQ ID NO:74 | Pig Skin | $7 \times 10^{-7}$ |

*The peptides tested were biotinylated at the C-terminus of the amino acid binding sequences and an amidated cysteine was added to the C-terminus of the binding sequence.

Example 10

Preparation of a Peptide-Based-Carbon Black Hair Colorant

The purpose of this Example was to prepare a peptide-based-carbon black hair colorant by covalently linking the hair-binding peptide D21, given as SEQ ID NO:46, to the surface of carbon black particles. The surface of the carbon black particles was functionalized by reaction with 2,2'-azo-bis(2methylpropionamide)-dihydrochloride to introduce free amino groups. The functionalized carbon black particles were then covalently linked to the specific hair-binding peptide.

Functionalization of Carbon Black Surface:

Carbon black (Nipex® 160-IQ from Degussa, Allendale, N.J.), 2.0 g, and 1.0 g of 2,2'-Azobis(2-methylpropionamide) dihydrochloride (Aldrich, Milwaukee, Wis.) were added to a 100 mL round-bottom flask and 30 mL of dioxane was added. The flask was purged with nitrogen for 5 min. Then, the flask was sealed with a rubber septum and the reaction mixture was stirred at 65° C. for 14 h. After this time, 50 mL of deionized water, prepared with a Nanopure water purification system (Barnstead/Thermolyne, Dubuque, Iowa), was added to the mixture. The diluted solution was centrifuged to collect the functionalized carbon black particles and to remove the organic solvent and unreacted reagents. The carbon black particles were washed with deionized water and centrifuged. This washing and centrifuging process was repeated 2 more times. The functionalized carbon black particles were then dried by lyophilization.

Synthesis of t-Boc-Protected Hair-Binding Peptide from Phage Clone D21

The purpose of this reaction was to protect the amino end group of the hair-binding peptide. The hair-binding peptide from phage clone D21 (0.25 g), given as SEQ ID NO:46 (95% purity, obtained from SynPep, Dublin, Calif.) was mixed with 2.5 mL of deionized water in a 25 mL round-bottom flask. Then, 20 mg of NaOH and 0.25 mL of t-butyl alcohol were added. After stirring the mixture for 2 min, 0.12 g of di-tert-butyl dicarbonate (t-Boc anhydride) (Aldrich) was added dropwise. The flask was sealed with a rubber septum and the reaction mixture was stirred overnight at room temperature. The reaction mixture was clear at the beginning of the reaction and became cloudy and then, precipitated after 1 h. Upon addition of water (10 mL), the reaction mixture formed a milky emulsion, which was then extracted three times with 5 mL portions of methylene chloride. The organic layer was washed twice with 5 mL portions of deionized water. The clear water layers were all combined and dried by lyophilization, yielding 0.20 g of a fluffy white powder (80% yield). The product was analyzed by liquid chromatography-mass spectrometry (LC-MS) and was found to have a molecular weight of 1323 g/mol, with a purity of 90% by weight.

Coupling of Amino-Functionalized Carbon Black with t-Boc-D21-Peptide:

Amino-functionalized carbon black (87 mg), t-Boc-D21-peptide (80 mg) and dicyclohexyl carbodiimide (22 mg) were added to 3 mL of tetrahydrofuran (THF). A solution of dimethyl aminopyridine (17 µL) in several drops of THF was added dropwise to this mixture with stirring. The resulting dark suspension was heated to 40° C. for 6 h with stirring, followed by stirring overnight at room temperature. Trifluoroacetic acid (0.6 mL) was added to the product and the mixture was stirred for another 6 h. Then, 5 mL of deionized water was added to the reaction mixture. The mixture was centrifuged at 3,500 rpm for 2 min and the supernatant was decanted. The solid remaining in the centrifuge tube was washed with deionized water and centrifuged again. This washing was repeated until the pH of supernatant reached approximately 6.0. The dark residue was then dried using a lyophilizer for 2 days, yielding a dark powder.

Example 11

Hair Dyeing Using a Peptide-Based-Carbon Black Hair Colorant

The purpose of this Example was to dye a sample of natural white hair using the peptide-based-carbon black hair colorant prepared in Example 10.

A bundle of natural white hair (approximately 100 pieces) (from International Hair Importers and Products Inc., Bellerose, N.Y.) was cleaned by mixing with 10 mL of 50% isopropanol for 30 min and then washed at least 5 times with distilled water. After drying in air, the cleaned hair was immersed for 30 min in a solution containing 50 mg of the hair-binding D21 peptide-carbon black hair colorant, described in Example 10, dissolved in 10 mL of distilled water. After dying, the hair was washed at least 5 times with distilled water. The original natural white hair became light black. The dyed hair was washed three times with a 30% shampoo solution (Pantene Pro-V shampoo) by immersing the hair in the shampoo solution and stirring with a glass pipette. The hair was then rinsed at least 10 times with distilled water. The final color of the dyed, natural white hair was very light black.

Example 12

Preparation of a Peptide-Based Hair Conditioner

The purpose of this Example was to prepare a peptide-based hair conditioner by covalently linking the hair-binding D21 peptide, given as SEQ ID NO:46, with behenyl alcohol using carbodiimide coupling.

Behenyl alcohol (Aldrich), 81.7 mg, and 62.0 mg of dicyclohexyl carbodiimide (DCC) were dissolved in 2.0 mL of THF in a 25 mL round-bottom flask. A solution containing 0.25 g of the 9-fluorenylmethyloxycarbonyl (Fmoc) N-terminal protected form of SEQ ID NO:46 (95% purity, obtained from SynPep, Dublin, Calif.) in 2.0 mL dimethylormamide (DMF) was added to the above mixture. Then, 50 µL of dimethylaminopyridine (DMAP) was added to the reaction mixture. With stirring, the reaction mixture was maintained at 40° C. for 3 h, and then at room temperature overnight. Then the solvent was evaporated under vacuum at room temperature for 4 h. After this time, the mixture was dissolved in 25 mL of ethyl acetate, and the unreacted peptide was extracted 3 times with water using 10 mL of deionized water for each extraction. The ethyl acetate phase was isolated and the ethyl acetate was removed using a rotary evaporator. The resulting solid product was dissolved in a solvent consisting of 2.5 mL of THF and 2.5 mL of DMF, and 1.5 mL of piperidine was added to deblock the amino group of the D21 peptide. This mixture was stirred for 2 h at room temperature and then the solvents were removed by rotary evaporation under vacuum. The final product was characterized by LC/MS.

Example 13

Preparation of a Peptide-Based Hair Conditioner

The purpose of this Example was to prepare a peptide-based hair conditioner by covalently linking the hair-binding, cysteine-attached D21 peptide, given as SEQ ID NO:64, with octylamine using the heterobifunctional cross-linking agent 3-maleimidopropionic acid N-hydroxysuccinimide ester.

Octylamine, obtained from Aldrich (Milwaukee, Wis.) was diluted by adding 11.6 mg to 0.3 mL of DMF. This diluted solution was added to a stirred solution containing 25 mg of 3-maleimidopropionic acid N-hydroxysuccinimide ester (Aldrich) and 5 mg of diisopropylethylamine (Aldrich) in 0.2 mL of DMF in a 5 mL round bottom flask. The reaction mixture turned turbid immediately and then became clear several minutes later. The solution was stirred for another 4 h. The solution was then dried under high vacuum. The product, octylamine-attached maleimidopropionate, was purified by column chromatography using a Silica gel 60 (EMD Chemicals, formerly EM Science, Gibbstown, N.J.) column and DMF/ether as the eluent.

Approximately 12 mg of the above product was placed into a 5 mL round bottom flask and 50 mg of cysteine-attached D21 peptide (obtained from SynPep, Dublin, Calif.), given as SEQ ID NO:64, and 0.5 mL of 0.1 M phosphate buffer at pH 7.2 were added. The cysteine-attached D21 peptide has 3 glycine residues and a cysteine attached to the end of the peptide binding sequence of the hair-binding D21 peptide (SEQ ID NO:46). This mixture was stirred at room temperature for 6 h. The final product, the C8-D21 peptide hair conditioner, was purified by extraction with water/ether.

Example 14

Preparation of a Peptide-Based-Carbon Black Hair Colorant

The purpose of this Example was to prepare a peptide-based carbon black hair colorant using carbon black that was functionalized with ethanol amine. The number of peptides attached to the carbon black surface was estimated from chemical analyses.

Preparation of Acid Functionalized Carbon Black Particles:

In a 1,000 mL beaker was added 25.5 g of carbon black (Nipex-160-IQ from Degussa, 100 g of ammonium persulfate [$(NH_4)_2S_2O_8$] (98% from Aldrich), and 333 mL of 1.0 M $H_2SO_4$ (98%, GR grade from EMD Chemicals) aqueous solution. The mixture was stirred with a magnetic stir plate for 24 h at room temperature. After this time, the reaction mixture was transferred to a 500 mL plastic centrifuge tube and centrifuged at 8,500 rpm for 20 min. The supernatant became clear and was removed. The product was washed 6 times with deionized water using centrifugation to collect the product after each wash. The final product was neutral (pH=6.0) and was dried by lyophilization for 24 h. The average size of the functionalized carbon black particles was 100 nm, as measured using a particle size analyzer (Microtrac Ultrafine Particle Analyzer, Microtrac Inc., Montgomeryville, Pa.).

Preparation of Amino-Functionalized Carbon Black Using Ethanolamine:

Two grams of the dried, acid functionalized carbon black, 25 mL of ethanolamine (99% from Aldrich) and 1 mL of concentrated $H_2SO_4$ (98%, GR grade from EMD Chemicals) were mixed in a 100 mL round bottom flask. The mixture was stirred rapidly with a magnetic stirrer and refluxed for 6 h. After the mixture cooled to room temperature, a sufficient amount of ammonium hydroxide (28.0-30.0% of $NH_3$ from EMD Chemicals) was added to neutralize the mixture. Then, the mixture was centrifuged and washed with water, as described in Example 6. The final product was neutral (pH=6.0) and was dried by lyophilization for 24 h. The dried, amino functionalized carbon black was readily dispersed in water.

The surface composition of the functionalized carbon black was analyzed by ESCA at the DuPont Corporate Center for Analytical Science. In ESCA, monoenergetic X-rays are focused onto the surface of a material to excite surface atoms. Core and valence shell electrons with energies characteristic of elements in the top 10 nm of the surface are ejected and their energy analyzed to obtain qualitative and quantitative information on surface composition. The kinetic energy of the electrons emitted provides information about the functional groups and oxidation states of the surface species. In this Example, the X-ray source used was a magnesium anode with an energy of 1253.6 eV. The samples were analyzed at a 45 degree exit angle (approximately 5 to 10 nm sampling depth). The ESCA analysis results are shown in Table 14. For ethanolamine-functionalized carbon black, the surface was mainly composed of unreacted —COOH groups and —C(=O)—OCH$_2$CH$_2$NH$_2$ groups. To calculate the ratio of amine (y) to carboxylic acid groups (x), a simple equation was used, specifically, y/(x+y)=(N %/14)/(O %/32) for ethanolamine. The results are given in Table 14.

TABLE 14

Results of ESCA Analysis of Functionalized Carbon Black

| Sample | C % | O % | N % | S % | —NH$_2$/—COOH |
|---|---|---|---|---|---|
| Acid Functionalized Carbon Black | 89 | 10 | ND* | 0.1 | 0 |
| Ethanolaminie Functionalized Carbon Black | 87 | 10 | 2.6 | ND | 1.47 |

*ND means not detectable

Coupling of Amino-Functionalized Carbon Black with t-Boc-D21-Peptide:

The amino-functionalized carbon black particles were then covalently linked to the specific hair-binding peptide D21, given as SEQ ID NO:46. The t-Boc protected D21 peptide was synthesized as described in Example 10. Then, amino-functionalized carbon black (87 mg), t-Boc-D21-peptide (80 mg) and dicyclohexyl carbodiimide (DCC) (22 mg) were added to 3 mL of tetrahydrofuran (THF). A solution of dimethylaminopyridine (DMAP) (17 µL) in several drops of THF was added dropwise to this mixture with stirring. The resulting dark suspension was heated to 40° C. for 6 h with stirring, followed by stirring overnight at room temperature. To remove the t-Boc protecting group from the D21 peptide, trifluoroacetic acid (TFA) (0.6 mL) was added to the product and the mixture was stirred for another 6 h. Then, 5 mL of deionized water was added to the reaction mixture. The mixture was centrifuged at 3,500 rpm for 2 min and the supernatant was decanted. The solid remaining in the centrifuge tube was washed with deionized water and centrifuged again. This washing was repeated until the pH of supernatant reached approximately 6.0. The dark residue was then dried using a lyophilizer for 2 days, yielding a dark powder.

The amino-functionalized carbon black particles and the peptide-linked carbon black particles were analyzed by ESCA, elemental analysis, and TGA (thermogravimetric analysis). The analytical results showed that the organic layer on the carbon black modified with ethanolamine was approximately 12% of the total weight. After the D21 peptides were attached to the carbon black particles, the peptide weight percentage was in the range of 18-30%. Therefore, for a 100 nm carbon black particle, a total of $9.5 \times 10^4$ molecules were attached to the surface after reacting with ethanolamine, and a total of 7,700 D21 peptide molecules were attached to the carbon black surface after reaction with the peptide. A calculation of the peptide density on the carbon black surface, revealed that each D21 peptide occupied 4 nm$^2$, which is comparable to the peptide density attached to the phage, approximately 12 nm$^2$.

Example 15

Specificity of the Peptide-Based-Carbon Black Hair Colorant

The purpose of this Example was to demonstrate the specificity of the D21 peptide-carbon black hair colorant.

The D21 peptide-based-carbon black colorant was prepared as described in Example 14.

A piece of pig skin (10 cm×10 cm), obtained from a local supermarket, was cleaned by mixing with 30 mL of 30% isopropanol for 10 min and then washed at least 5 times with distilled water. After drying in air, the cleaned pig skin was immersed in a plate holder with multiple wells containing a solution of 50 mg of the D21 peptide-carbon black colorant dissolved in 10 mL of distilled water. After applying the colorant for 15 min, the pig skin was washed three times with a 30% shampoo solution (Pantene Pro-V shampoo) by dropping the shampoo solution into the wells and decanting it. Then, the pig skin was rinsed 5 times with distilled water.

A normal white hair sample, obtained from International Hair Importers and Products (Bellerose, N.Y.), was treated in the same manner as the pig skin.

After washing, the pig skin showed negligible dark color, while the hair was very light black. These results demonstrate that the D21 peptide-carbon black colorant has specific binding to hair, but not to skin.

Example 16

Preparation of a Peptide-Polysiloxane Hair Conditioner

The purpose of this Example was to synthesize a D21 peptide-polysiloxane hair conditioner. The reactive side functional groups of the D21 peptide, given as SEQ ID NO:46, were fully protected so that the reaction with the polysiloxane proceeded only with the C-terminal group of the peptide. In addition, a tripeptide spacer, consisting of glycine residues, was added to the C-terminal end of the binding sequence.

Fifty milligrams of the fully protected D21 peptide Fmoc-R(Pbf)T(tBu)N(Trt)MD(OtBu)H(Trt)PMVT(tBu)GGG (where Fmoc means fluorenylmethoxyl carbonyl; Pbf means 2,2,6,4,7-pentamethyldihydrobenzofuran-5-sulfonyl; tBu means t-butyl; Trt means trityl; and Otbu means t-butoxyl) (MW 2522, 0.02 mmol, 95% purity from SynPep, Dublin, Calif.), given as SEQ ID NO:78 was dissolved in 1 mL of dimethylormamide (DMF, from E. Merck, Darmstadt, Germany) in a 5 mL round bottom flask. Polysiloxane fluid 2-8566 (77 mg) (N %=0.875%, 0.024 mmol of —$NH_2$, from Dow Corning, Midland, Mich.) was dissolved in 2 mL of THF (E. Merck) in a sample vial, then transferred into the round bottom flask containing the peptide solution. Then, 5 mg of dicyclohexyl carbodiimide (DCC, 0.024 mmol) and 5 μL of dimethylaminopyridine (DMAP) were added to the flask. The flask was sealed with a rubber stopper and the reaction mixture was stirred at 50° C. for 5 h and then, at room temperature overnight. After the reaction was completed, the solvent was pumped out under vacuum. After drying, 122 mg of the solid product was obtained. The yield was about 90%.

The solid product was dissolved in N,N-dimethylacetamide (DMAC, from EMD Chemicals) and 5 mg/mL of the product solution in DMAC was prepared for GPC (gel permeation chromatography) analysis with refractive index detection to determine the molecular weight. The original polysiloxane (Dow Corning 2-8566) was not soluble in DMAC and was not observed in the separation region of the chromatogram. The D21 peptide had a sharp, low molecular weight peak, and the product sample contained 2 peaks, one from the free D21 peptide and a broad peak, which was attributed to polysiloxane grafted with D21 peptide. The weight-average molecular weight ($M_W$) was calculated from polymethylmethacrylate (PMMA) standards. The $M_W$ of D21 peptide and the peptide-polysiloxane conditioner were $4.7 \times 10^3$, and $4.4 \times 10^4$, respectively.

A cleavage reagent (which is named Reagent K by SynPep) having the following composition: trifluoroacetic acid/$H_2O$/thioanisole/ethanedithiol/phenol (85:5:5:2.5:2.5, by volume) was used to cleave the protecting groups from the side functional groups of the D21 peptide. Reagent K (1 mL) was pre-cooled to −20° C. and then, added to 100 mg of the D21 peptide-polysiloxane conditioner. The mixture was stirred for 3-4 h at room temperature and then Reagent K was removed under high vacuum. Then, the Fmoc protecting group was removed from the N-terminus of the peptide by adding 61.2 mg of 20 vol % piperidine in DMF to the mixture and stirring for 30 min, followed by pumping under high vacuum. The final product was not completely soluble in THF, DMF, or DMAC. GPC analysis of the final product was not possible because of the low solubility.

Example 17

Effectiveness of Peptide-Based Hair Conditioner

The purpose of this Example was to demonstrate the effectiveness of a peptide-based hair conditioner in reducing frictional forces in human hair fibers and to compare its performance against a commercial conditioning agent. Fiber friction is a significant contributor to combing behavior of hair fiber assemblies (i.e., multiple fibers). The single hair fiber characterization of frictional forces can be related to the combing behavior of the hair assembly. Interfiber friction studies illustrate the improvement to the hair surface from conditioner applications. The lower the interfiber friction, the smoother the hair looks and feels, and the easier it is to comb. The interfiber friction measurement method employed in this Example is one of a few hair fiber tests to give hard, quantitative data and is generally accepted in the industry.

The peptide-based hair conditioner described in Example 12, which consists of the hair-binding peptide given as SEQ ID NO:46 covalently linked to behenyl alcohol, was used in a formulation consisting of a mixture of 0.25% by weight of the peptide-based conditioner and 1.5% by weight of Performix™ Lecithin (ADM Lecithin, Decatur. Ill.) in distilled water. The aqueous solution was mixed at 7000 rpm for 4 min using a Silverson L4RT-A High Shear Laboratory Mixer (Silverson Machines, Inc., East Longmeadow, Mass.) with a general purpose disintegrating head and a 0.95 cm mini-micro tubular frame. A 0.5% solution of Dow Dow Corning® 929 Cationic Emulsion (Dow Corning Corp., Midland, Mich.), a commercial conditioning agent, in distilled water was prepared using identical mixing conditions.

European dark brown hair switches (International Hair Importers and Products) were cleaned before testing by immersing in isopropanol for 30 min, then washing 10 times with distilled water. Single hair fibers from these switches were sent to Textile Research Institute (TRI), Princeton, N.J., for friction testing. At TRI, the hair fibers were immersed in the conditioner solutions for 5 min at approximately 35° C. without agitation. Afterwards, they were rinsed for 1 min in lukewarm water and then dried overnight at 21° C. and 65% relative humidity.

Frictional force measurements of treated hair fibers were measured by the Interfiber friction test using a single-fiber friction apparatus, as describe by Kamath et al. (*J. Appl. Polymer Sci.*, 85:394-414 (2002)). Hair fibers were evaluated at high normal forces (high load) (0.74 g) against a chromed steel wire, crosshead speed of 1 mm/min, using an Instron Tensile Testing machine. And low normal forces (low load) (8.5 mg) were measured against another single hair fiber using the TRI/Scan™ Surface Force Analyzer (Textile Research Institute). This apparatus measures small forces with a Cahn® microbalance (mass resolution of 0.1 mg) and features a computer controlled stage. The results of these measurements are given in Table 15.

TABLE 15

Results of Friction Measurments
Friction Force (F_f)

| Low Load | Cationic Emulsion F_f (mg) | Peptide Conditioner F_f (mg) | High Load | Cationic Emulsion F_f (g) | Peptide Conditioner F_f (g) |
|---|---|---|---|---|---|
| Fiber 1 | 1.392 | 0.294 | Fiber 1 | 0.065 | 0.070 |
| Fiber 2 | 1.126 | 0.213 | Fiber 2 | 0.043 | 0.051 |
| Fiber 3 | 0.937 | 0.486 | Fiber 3 | 0.109 | 0.041 |
| Fiber 4 | 1.644 | 0.221 | Fiber 4 | 0.108 | 0.057 |
| Mean | 1.275 | 0.304 | | 0.081 | 0.055 |

The peptide-based conditioner had a lower average friction than the Dow Corning® 929 Cationic Emulsion conditioner in both cases. Subsequently, a conditioning sample of 1.5% lecithin was tested for fiber friction (low load) and the average mean frictional force was 3.366 mg, indicating that the conditioning effects observed with the peptide-based conditioner was not due to the presence of the lecithin in the formulation. These results demonstrate the effectiveness of the peptide-based hair conditioner.

What is claimed is:

1. A diblock, peptide-based skin conditioner having the general structure $(SBP)_n$-SCA, wherein
  a) SBP is a skin-binding peptide;
  b) SCA is a skin conditioning agent; and
  c) n ranges from 1 to about 50;
wherein the skin binding peptide is from about 7 to about 25 amino acids and has a binding affinity for skin, as measured as $MB_{50}$, equal to or less than $10^{-5}$ M.

2. A diblock, peptide-based skin colorant having the general structure $(SBP)_n$-C, wherein
  a) SBP is a skin-binding peptide;
  b) C is a coloring agent; and
  c) n ranges from 1 to about 500;
wherein the skin binding peptide is from about 7 to about 25 amino acids and has a binding affinity for skin, as measured as $MB_{50}$, equal to or less than $10^{-5}$ M.

3. A triblock, peptide-based skin conditioner having the general structure $[(SBP)_m\text{-}S]_n$-SCA, wherein
  a) SBP is a skin-binding peptide;
  b) SCA is a skin conditioning agent;
  c) S is a spacer;
  d) m ranges from 1 to about 50; and
  e) n ranges from 1 to about 50;
wherein the skin binding peptide is from about 7 to about 25 amino acids and has a binding affinity for skin, as measured as $MB_{50}$, equal to or less than $10^{-5}$ M.

4. A triblock, peptide-based skin colorant having the general structure $[(SBP)_m\text{-}S]_n$-C, wherein
  a) SBP is a skin-binding peptide;
  b) C is a coloring agent;
  c) S is a spacer;
  d) m ranges from 1 to about 50; and
  e) n ranges from 1 to about 500;
wherein the skin binding peptide is from about 7 to about 25 amino acids and has a binding affinity for skin, as measured as $MB_{50}$, equal to or less than $10^{-5}$ M.

5. The peptide-based conditioner or colorant of claim 1, 2, 3 or 4 wherein the skin-binding peptide is from about 7 to about 20 amino acids.

6. The peptide-based conditioner or colorant of claim 1, 2, 3 or 4 wherein the skin-binding peptide is from about 7 to about 12 amino acids.

7. The peptide-based conditioner or colorant of claim 1, 2, 3 or 4 wherein the skin-binding peptide further comprises a cysteine residue on at least one end of the peptide sequence.

8. The peptide-based skin conditioner or the peptide-based skin colorant of claim 1, 2, 3 or 4 wherein the skin-binding peptide has the amino acid sequence selected from the group consisting of SEQ ID NO:2 and 61.

9. The peptide-based skin conditioner of claim 1 or 3 wherein the skin conditioning agent is selected from the group consisting of polysalicylates, propylene glycol, glycerin, glycolic acid, lactic acid, malic acid, citric acid, tartaric acid, glucaric acid, galactaric acid, 3-hydroxyvaleric acid, salicylic acid, and 1,3 propanediol.

10. The peptide-based skin colorant of claim 2 or 4 wherein the coloring agent is selected from the group consisting of D&C Red No. 21, D&C Red No. 27, D&C Red Orange No. 5, D&C Red No. 21, D&C Orange No. 10, titanium dioxide, zinc oxide, D&C Red No. 36, D&C Orange No. 17, the calcium lakes of D&C Red Nos. 7, 11, 31, 34, the barium lake of D&C Red No. 12, the strontium lake D&C Red No. 13, the aluminum lake of FD&C Yellow No. 5, the aluminum lake of FD&C Yellow No. 6, the aluminum lake of D&C Red No. 27, the aluminum lake of D&C Red No. 21, the aluminum lake of FD&C Blue No. 1, iron oxides, manganese violet, chromium oxide, ultramarine blue, carbon black, and dihydroxyacetone.

11. The peptide-based conditioner or colorant of claim 3 or 4 wherein the spacer is selected from the group consisting of ethanol amine, ethylene glycol, polyethylene with a chain length of 6 carbon atoms, polyethylene glycol with 3 to 6 repeating units, phenoxyethanol, propanolamide, butylene glycol, butyleneglycolamide, propyl phenyl, ethyl alkyl chain, propyl alkyl chain, hexyl alkyl chain, steryl alkyl chains, cetyl alkyl chains, and palmitoyl alkyl chains.

12. The peptide-based conditioner or colorant of claim 3 or 4 wherein the spacer is a peptide comprising amino acids selected from the group consisting of glycine, alanine, serine, and mixtures thereof.

13. A skin care composition comprising an effective amount of the peptide-based skin conditioner of claim 1 or 3.

14. A cosmetic composition comprising an effective amount of the peptide-based skin colorant of claim 2 or 4.

15. A method for forming a protective layer of a peptide-based conditioner on skin or lips comprising applying the composition of claim 9 to the skin or lips and allowing the formation of said protective layer.

16. A method for coloring skin or lips comprising applying the cosmetic composition of claim 14 to the skin or lips.

\* \* \* \* \*

UNITED STATES PATENT AND TRADEMARK OFFICE
CERTIFICATE OF CORRECTION

PATENT NO. : 7,666,397 B2 Page 1 of 1
APPLICATION NO. : 11/592108
DATED : February 23, 2010
INVENTOR(S) : Huang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 136 days.

Signed and Sealed this

Seventh Day of December, 2010

David J. Kappos
*Director of the United States Patent and Trademark Office*

SEQUENCE LISTING

<160> NUMBER OF SEQ ID NOS: 104

<210> SEQ ID NO 1
<211> LENGTH: 8
<212> TYPE: PRT
<213> ORGANISM: Artificial Sequence
<220> FEATURE:
<223> OTHER INFORMATION: Hair-binding peptide

<400> SEQUENCE: 1

Leu Glu Ser Thr Pro Lys Met Lys
1               5

<210> SEQ ID NO 2
<211> LENGTH: 7
<212> TYPE: PRT
<213> ORGANISM: Artificial Sequence
<220> FEATURE:
<223> OTHER INFORMATION: Skin-binding peptide

<400> SEQUENCE: 2

Phe Thr Gln Ser Leu Pro Arg
1               5

<210> SEQ ID NO 3
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 3

Ser Val Ser Val Gly Met Lys Pro Ser Pro Arg Pro
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 4

Leu Asp Val Glu Ser Tyr Lys Gly Thr Ser Met Pro
1               5                   10

<210> SEQ ID NO 5
<211> LENGTH: 12
<212> TYPE: PRT

```
<213> ORGANISM: Artificial Sequence
<220> FEATURE:
<223> OTHER INFORMATION: Hair-binding peptide.

<400> SEQUENCE: 5

Arg Val Pro Asn Lys Thr Val Thr Val Asp Gly Ala
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 6

Asp Arg His Lys Ser Lys Tyr Ser Ser Thr Lys Ser
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 7

Lys Asn Phe Pro Gln Gln Lys Glu Phe Pro Leu Ser
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 8

Gln Arg Asn Ser Pro Pro Ala Met Ser Arg Arg Asp
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 9

Thr Arg Lys Pro Asn Met Pro His Gly Gln Tyr Leu
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 10

Lys Pro Pro His Leu Ala Lys Leu Pro Phe Thr Thr
1               5                   10

<210> SEQ ID NO 11
<211> LENGTH: 12
<212> TYPE: PRT
<213> ORGANISM: Artificial Sequence
```

```
<220> FEATURE:
<223> OTHER INFORMATION: Hair-binding peptide

<400> SEQUENCE: 11

Asn Lys Arg Pro Pro Thr Ser His Arg Ile His Ala
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 12

Asn Leu Pro Arg Tyr Gln Pro Pro Cys Lys Pro Leu
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 13

Arg Pro Pro Trp Lys Lys Pro Ile Pro Pro Ser Glu
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 14

Arg Gln Arg Pro Lys Asp His Phe Phe Ser Arg Pro
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Hair-binding peptide
<220> FEATURE:
<221> NAME/KEY: MISC_FEATURE
<222> LOCATION: (6)..(6)
<223> OTHER INFORMATION: Xaa = Thr or Pro
<220> FEATURE:
<221> NAME/KEY: MISC_FEATURE
<222> LOCATION: (12)..(12)
<223> OTHER INFORMATION: Xaa = Glu or Ala

<400> SEQUENCE: 15

Ser Val Pro Asn Lys Xaa Val Thr Val Asp Gly Xaa
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 16

Thr Thr Lys Trp Arg His Arg Ala Pro Val Ser Pro
```

```
1               5                   10
```

<210> SEQ ID NO 17
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 17

```
Trp Leu Gly Lys Asn Arg Ile Lys Pro Arg Ala Ser
1               5                   10
```

<210> SEQ ID NO 18
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 18

```
Ser Asn Phe Lys Thr Pro Leu Pro Leu Thr Gln Ser
1               5                   10
```

<210> SEQ ID NO 19
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 19

```
Lys Glu Leu Gln Thr Arg Asn Val Val Gln Arg Glu
1               5                   10
```

<210> SEQ ID NO 20
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 20

```
Thr Pro Thr Ala Asn Gln Phe Thr Gln Ser Val Pro
1               5                   10
```

<210> SEQ ID NO 21
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 21

```
Ala Ala Gly Leu Ser Gln Lys His Glu Arg Asn Arg
1               5                   10
```

<210> SEQ ID NO 22
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 22

```
Glu Thr Val His Gln Thr Pro Leu Ser Asp Arg Pro
1               5                   10
```

<210> SEQ ID NO 23
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 23

Leu Pro Ala Leu His Ile Gln Arg His Pro Arg Met
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 24

Gln Pro Ser His Ser Gln Ser His Asn Leu Arg Ser
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 25

Arg Gly Ser Gln Lys Ser Lys Pro Pro Arg Pro Pro
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 26

Thr His Thr Gln Lys Thr Pro Leu Leu Tyr Tyr His
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 27

Thr Lys Gly Ser Ser Gln Ala Ile Leu Lys Ser Thr
1               5                   10

<210> SEQ ID NO 28
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 28

Asp Leu His Thr Val Tyr His
1               5

```
<210> SEQ ID NO 29
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 29

His Ile Lys Pro Pro Thr Arg
1               5

<210> SEQ ID NO 30
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 30

His Pro Val Trp Pro Ala Ile
1               5

<210> SEQ ID NO 31
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 31

Met Pro Leu Tyr Tyr Leu Gln
1               5

<210> SEQ ID NO 32
<211> LENGTH: 26
<212> TYPE: PRT
<213> ORGANISM: Artificial Sequence
<220> FEATURE:
<223> OTHER INFORMATION: Hair-binding peptide

<400> SEQUENCE: 32

His Leu Thr Val Pro Trp Arg Gly Gly Gly Ser Ala Val Pro Phe Tyr
1               5                   10                  15

Ser His Ser Gln Ile Thr Leu Pro Asn His
            20                  25

<210> SEQ ID NO 33
<211> LENGTH: 41
<212> TYPE: PRT
<213> ORGANISM: Artificial Sequence
<220> FEATURE:
<223> OTHER INFORMATION: Hair-binding peptide

<400> SEQUENCE: 33

Gly Pro His Asp Thr Ser Ser Gly Gly Val Arg Pro Asn Leu His His
1               5                   10                  15

Thr Ser Lys Lys Glu Lys Arg Glu Asn Arg Lys Val Pro Phe Tyr Ser
            20                  25                  30

His Ser Val Thr Ser Arg Gly Asn Val
        35                  40

<210> SEQ ID NO 34
<211> LENGTH: 7
<212> TYPE: PRT
<213> ORGANISM: Artificial Sequence
```

```
<220> FEATURE:
<223> OTHER INFORMATION: Hair-binding peptide

<400> SEQUENCE: 34

Lys His Pro Thr Tyr Arg Gln
1               5

<210> SEQ ID NO 35
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 35

His Pro Met Ser Ala Pro Arg
1               5

<210> SEQ ID NO 36
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 36

Met Pro Lys Tyr Tyr Leu Gln
1               5

<210> SEQ ID NO 37
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 37

Met His Ala His Ser Ile Ala
1               5

<210> SEQ ID NO 38
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 38

Thr Ala Ala Thr Thr Ser Pro
1               5

<210> SEQ ID NO 39
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 39

Leu Gly Ile Pro Gln Asn Leu
1               5

<210> SEQ ID NO 40
<211> LENGTH: 12
<212> TYPE: PRT
<213> ORGANISM: Artificial Sequence
<220> FEATURE:
```

<223> OTHER INFORMATION: Hair-binding peptide

<400> SEQUENCE: 40

Ala Lys Pro Ile Ser Gln His Leu Gln Arg Gly Ser
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 41

Ala Pro Pro Thr Pro Ala Ala Ala Ser Ala Thr Thr
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 42

Asp Pro Thr Glu Gly Ala Arg Arg Thr Ile Met Thr
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 43

Glu Gln Ile Ser Gly Ser Leu Val Ala Ala Pro Trp
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 44

Leu Asp Thr Ser Phe Pro Pro Val Pro Phe His Ala
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Hair-binding peptide

<400> SEQUENCE: 45

Leu Pro Arg Ile Ala Asn Thr Trp Ser Pro Ser
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Hair-binding peptide

```
<400> SEQUENCE: 46

Arg Thr Asn Ala Ala Asp His Pro Ala Ala Val Thr
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 47

Ser Leu Asn Trp Val Thr Ile Pro Gly Pro Lys Ile
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 48

Thr Asp Met Gln Ala Pro Thr Lys Ser Tyr Ser Asn
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 49

Thr Ile Met Thr Lys Ser Pro Ser Leu Ser Cys Gly
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 50

Thr Pro Ala Leu Asp Gly Leu Arg Gln Pro Leu Arg
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 51

Thr Tyr Pro Ala Ser Arg Leu Pro Leu Leu Ala Pro
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Hair-binding peptide
```

```
<400> SEQUENCE: 52

Ala Lys Thr His Lys His Pro Ala Pro Ser Tyr Ser
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Hair-binding and nail-binding peptide

<400> SEQUENCE: 53

Tyr Pro Ser Phe Ser Pro Thr Tyr Arg Pro Ala Phe
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 54

Thr Asp Pro Thr Pro Phe Ser Ile Ser Pro Glu Arg
1               5                   10

<210> SEQ ID NO 55
<211> LENGTH: 20
<212> TYPE: PRT
<213> ORGANISM: Artificial Sequence
<220> FEATURE:
<223> OTHER INFORMATION: Hair-binding peptide

<400> SEQUENCE: 55

Cys Ala Ala Gly Cys Cys Thr Cys Ala Gly Cys Gly Ala Cys Cys Gly
1               5                   10                  15

Ala Ala Thr Ala
            20

<210> SEQ ID NO 56
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 56

Trp His Asp Lys Pro Gln Asn Ser Ser Lys Ser Thr
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 57

Asn Glu Val Pro Ala Arg Asn Ala Pro Trp Leu Val
1               5                   10

<210> SEQ ID NO 58
<211> LENGTH: 13
<212> TYPE: PRT
<213> ORGANISM: Artificial Sequence
<220> FEATURE:
```

-continued

<223> OTHER INFORMATION: Hair-binding peptide

<400> SEQUENCE: 58

Asn Ser Pro Gly Tyr Gln Ala Asp Ser Val Ala Ile Gly
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 59

Thr Gln Asp Ser Ala Gln Lys Ser Pro Ser Pro Leu
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Nail-binding peptide

<400> SEQUENCE: 60

Ala Leu Pro Arg Ile Ala Asn Thr Trp Ser Pro Ser
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Skin-binding peptide

<400> SEQUENCE: 61

Thr Pro Phe His Ser Pro Glu Asn Ala Pro Gly Ser
1               5                   10

<210> SEQ ID NO 62
<211> LENGTH: 20
<212> TYPE: DNA
<213> ORGANISM: Artificial Sequence
<220> FEATURE:
<223> OTHER INFORMATION: Primer

<400> SEQUENCE: 62
ccctcatagt tagcgtaacg                                          20

<210> SEQ ID NO 63
<211> LENGTH: 12
<212> TYPE: PRT
<213> ORGANISM: Artificial Sequence
<220> FEATURE:
<223> OTHER INFORMATION: Control peptide

<400> SEQUENCE: 63

Lys His Gly Pro Asp Leu Leu Arg Ser Ala Pro Arg
1               5                   10

<210> SEQ ID NO 64
<211> LENGTH: 16
<212> TYPE: PRT
<213> ORGANISM: Artificial Sequence
<220> FEATURE:
<223> OTHER INFORMATION: Cysteine-attached hair-binding peptide

```
<400> SEQUENCE: 64

Arg Thr Asn Ala Ala Asp His Pro Ala Ala Val Thr Gly Gly Gly Cys
1               5                   10                  15

<210> SEQ ID NO 65
<211> LENGTH: 8
<212> TYPE: PRT
<213> ORGANISM: Artificial Sequence
<220> FEATURE:
<223> OTHER INFORMATION: Caspase 3 cleavage site

<400> SEQUENCE: 65

Leu Glu Ser Gly Asp Glu Val Asp
1               5

<210> SEQ ID NO 66
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 66

Thr Pro Pro Glu Leu Leu His Gly Asp Pro Arg Ser
1               5                   10

<210> SEQ ID NO 67
<211> LENGTH: 20
<212> TYPE: DNA
<213> ORGANISM: Artificial Sequence
<220> FEATURE:
<223> OTHER INFORMATION: Primer

<400> SEQUENCE: 67
caagcctcag cgaccgaata                                            20

<210> SEQ ID NO 68
<211> LENGTH: 23
<212> TYPE: DNA
<213> ORGANISM: Artificial Sequence
<220> FEATURE:
<223> OTHER INFORMATION: Primer

<400> SEQUENCE: 68
cgtaacactg agtttcgtca cca                                        23

<210> SEQ ID NO 69
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 69

Thr Pro Pro Thr Asn Val Leu Met Leu Ala Thr Lys
1               5                   10

<210> SEQ ID NO 70
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 70

Asn Thr Ser Gln Leu Ser Thr
1               5
```

```
1               5
```

<210> SEQ ID NO 71
<211> LENGTH: 14
<212> TYPE: PRT
<213> ORGANISM: Artificial Sequence
<220> FEATURE:
<223> OTHER INFORMATION: Biotinylated hair-binding peptide
<220> FEATURE:
<221> NAME/KEY: MISC_FEATURE
<222> LOCATION: (13)..(13)
<223> OTHER INFORMATION: Biotinylated
<220> FEATURE:
<221> NAME/KEY: MISC_FEATURE
<222> LOCATION: (14)..(14)
<223> OTHER INFORMATION: Amidated

<400> SEQUENCE: 71

```
Arg Thr Asn Ala Ala Asp His Pro Ala Ala Val Thr Lys Cys
1               5                   10
```

<210> SEQ ID NO 72
<211> LENGTH: 14
<212> TYPE: PRT
<213> ORGANISM: Artificial Sequence
<220> FEATURE:
<223> OTHER INFORMATION: Biotinylated hair-binding peptide
<220> FEATURE:
<221> NAME/KEY: MISC_FEATURE
<222> LOCATION: (13)..(13)
<223> OTHER INFORMATION: Biotinylated
<220> FEATURE:
<221> NAME/KEY: MISC_FEATURE
<222> LOCATION: (14)..(14)
<223> OTHER INFORMATION: Amidated

<400> SEQUENCE: 72

```
Ala Leu Pro Arg Ile Ala Asn Thr Trp Ser Pro Ser Lys Cys
1               5                   10
```

<210> SEQ ID NO 73
<211> LENGTH: 14
<212> TYPE: PRT
<213> ORGANISM: Artificial Sequence
<220> FEATURE:
<223> OTHER INFORMATION: Biotinylated hair-binding peptide
<220> FEATURE:
<221> NAME/KEY: MISC_FEATURE
<222> LOCATION: (13)..(13)
<223> OTHER INFORMATION: Biotinylated
<220> FEATURE:
<221> NAME/KEY: MISC_FEATURE
<222> LOCATION: (14)..(14)
<223> OTHER INFORMATION: Amidated

<400> SEQUENCE: 73

```
Thr Pro Pro Glu Leu Leu His Gly Asp Pro Arg Ser Lys Cys
1               5                   10
```

<210> SEQ ID NO 74
<211> LENGTH: 14
<212> TYPE: PRT
<213> ORGANISM: Artificial Sequence
<220> FEATURE:
<223> OTHER INFORMATION: Biotinylated skin-binding peptide
<220> FEATURE:
<221> NAME/KEY: MISC_FEATURE
<222> LOCATION: (13)..(13)
<223> OTHER INFORMATION: Biotinylated
<220> FEATURE:
<221> NAME/KEY: MISC_FEATURE
<222> LOCATION: (14)..(14)

<223> OTHER INFORMATION: Amidated

<400> SEQUENCE: 74

Thr Pro Phe His Ser Pro Glu Asn Ala Pro Gly Ser Lys Cys
1               5                   10

<210> SEQ ID NO 75
<211> LENGTH: 15
<212> TYPE: PRT
<213> ORGANISM: Artificial Sequence
<220> FEATURE:
<223> OTHER INFORMATION: Fully protected hair-binding peptide
<220> FEATURE:
<221> NAME/KEY: MISC_FEATURE
<222> LOCATION: (1)..(1)
<223> OTHER INFORMATION: Fluoroenylmethoxlcarbonyl (Fmoc)-protected
<220> FEATURE:
<221> NAME/KEY: MISC_FEATURE
<222> LOCATION: (1)..(1)
<223> OTHER INFORMATION: 2,2,6,4,7-pentamethyldihydrobenzofuran-
      5sulfonyl-protected
<220> FEATURE:
<221> NAME/KEY: MISC_FEATURE
<222> LOCATION: (2)..(2)
<223> OTHER INFORMATION: t-butyl-protected
<220> FEATURE:
<221> NAME/KEY: MISC_FEATURE
<222> LOCATION: (3)..(3)
<223> OTHER INFORMATION: Trityl-protected
<220> FEATURE:
<221> NAME/KEY: MISC_FEATURE
<222> LOCATION: (6)..(6)
<223> OTHER INFORMATION: t-butoxyl-protected
<220> FEATURE:
<221> NAME/KEY: MISC_FEATURE
<222> LOCATION: (7)..(7)
<223> OTHER INFORMATION: Trityl-protected
<220> FEATURE:
<221> NAME/KEY: MISC_FEATURE
<222> LOCATION: (12)..(12)
<223> OTHER INFORMATION: t-butyl-protected

<400> SEQUENCE: 75

Arg Thr Asn Ala Ala Asp His Pro Ala Ala Val Thr Gly Gly Gly
1               5                   10                  15

<210> SEQ ID NO 76
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 76

Asn Thr Pro Lys Glu Asn Trp
1               5

<210> SEQ ID NO 77
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 77

Asn Thr Pro Ala Ser Asn Arg
1               5

<210> SEQ ID NO 78
<211> LENGTH: 7
<212> TYPE: PRT

-continued

```
<213> ORGANISM: Artificial Sequence
<220> FEATURE:
<223> OTHER INFORMATION: Hair-binding peptide

<400> SEQUENCE: 78

Pro Arg Gly Met Leu Ser Thr
1               5

<210> SEQ ID NO 79
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 79

Pro Pro Thr Tyr Leu Ser Thr
1               5

<210> SEQ ID NO 80
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 80

Thr Ile Pro Thr His Arg Gln His Asp Tyr Arg Ser
1               5                   10

<210> SEQ ID NO 81
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 81

Thr Pro Pro Thr His Arg Leu
1               5

<210> SEQ ID NO 82
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 82

Leu Pro Thr Met Ser Thr Pro
1               5

<210> SEQ ID NO 83
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 83

Leu Gly Thr Asn Ser Thr Pro
1               5

<210> SEQ ID NO 84
<211> LENGTH: 12
<212> TYPE: PRT
<213> ORGANISM: Artificial Sequence
```

```
<220> FEATURE:
<223> OTHER INFORMATION: Hair-binding peptide

<400> SEQUENCE: 84

Thr Pro Leu Thr Gly Ser Thr Asn Leu Leu Ser Ser
1               5                   10

<210> SEQ ID NO 85
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 85

Thr Pro Leu Thr Lys Glu Thr
1               5

<210> SEQ ID NO 86
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 86

Gln Gln Ser His Asn Pro Pro
1               5

<210> SEQ ID NO 87
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 87

Thr Gln Pro His Asn Pro Pro
1               5

<210> SEQ ID NO 88
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 88

Ser Thr Asn Leu Leu Arg Thr Ser Thr Val His Pro
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 89

His Thr Gln Pro Ser Tyr Ser Ser Thr Asn Leu Phe
1               5                   10

<210> SEQ ID NO 90
<211> LENGTH: 7
<212> TYPE: PRT
<213> ORGANISM: Artificial Sequence
<220> FEATURE:
```

```
<223> OTHER INFORMATION: Hair-binding peptide

<400> SEQUENCE: 90

Ser Leu Leu Ser Ser His Ala
1               5

<210> SEQ ID NO 91
<211> LENGTH: 12
<212> TYPE: PRT
<213> ORGANISM: Artificial Sequence
<220> FEATURE:
<223> OTHER INFORMATION: Hair-binding peptide

<400> SEQUENCE: 91

Gln Gln Ser Ser Ile Ser Leu Ser Ser His Ala Val
1               5                   10

<210> SEQ ID NO 92
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 92

Asn Ala Ser Pro Ser Ser Leu
1               5

<210> SEQ ID NO 93
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 93

His Ser Pro Ser Ser Leu Arg
1               5

<210> SEQ ID NO 94
<211> LENGTH: 7
<212> TYPE: PRT
<213> ORGANISM: Artificial Sequence
<220> FEATURE:
<223> OTHER INFORMATION: Hair-binding peptide
<220> FEATURE:
<221> NAME/KEY: MISC_FEATURE
<222> LOCATION: (2)..(2)
<223> OTHER INFORMATION: Xaa = His, Arg, or Asn

<400> SEQUENCE: 94

Lys Xaa Ser His His Thr His
1               5

<210> SEQ ID NO 95
<211> LENGTH: 7
<212> TYPE: PRT
<213> ORGANISM: Artificial Sequence
<220> FEATURE:
<223> OTHER INFORMATION: Hair-binding peptide
<220> FEATURE:
<221> NAME/KEY: MISC_FEATURE
<222> LOCATION: (2)..(2)
<223> OTHER INFORMATION: Xaa = His, Arg, or Asn

<400> SEQUENCE: 95

Glu Xaa Ser His His Thr His
1               5
```

```
<210> SEQ ID NO 96
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 96

Leu Glu Ser Thr Ser Leu Leu
1               5

<210> SEQ ID NO 97
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 97

Thr Pro Leu Thr Lys Glu Thr
1               5

<210> SEQ ID NO 98
<211> LENGTH: 7
<212> TYPE: PRT
<213> ORGANISM: Artificial Sequence
<220> FEATURE:
<223> OTHER INFORMATION: Hair-binding peptide

<400> SEQUENCE: 98

Lys Gln Ser His Asn Pro Pro
1               5

<210> SEQ ID NO 99
<211> LENGTH: 12
<212> TYPE: PRT
<213> ORGANISM: Artificial Sequence
<220> FEATURE:
<223> OTHER INFORMATION: Skin-binding sequence

<400> SEQUENCE: 99

Lys Gln Ala Thr Phe Pro Pro Asn Pro Thr Ala Tyr
1               5                   10

<210> SEQ ID NO 100
<211> LENGTH: 12
<212> TYPE: PRT
<213> ORGANISM: Artificial Sequence
<220> FEATURE:
<223> OTHER INFORMATION: Skin-binding peptide

<400> SEQUENCE: 100

His Gly His Met Val Ser Thr Ser Gln Leu Ser Ile
1               5                   10

<210> SEQ ID NO 101
<211> LENGTH: 7
<212> TYPE: PRT
<213> ORGANISM: Artificial Sequence
<220> FEATURE:
<223> OTHER INFORMATION: Skin-binding peptide

<400> SEQUENCE: 101

Leu Ser Pro Ser Arg Met Lys
1               5
```

```
<210> SEQ ID NO 102
<211> LENGTH: 7
<212> TYPE: PRT
<213> ORGANISM: Artificial Sequence
<220> FEATURE:
<223> OTHER INFORMATION: Skin-binding peptide

<400> SEQUENCE: 102

Leu Pro Ile Pro Arg Met Lys
1               5

<210> SEQ ID NO 103
<211> LENGTH: 7
<212> TYPE: PRT
<213> ORGANISM: Artificial Sequence
<220> FEATURE:
<223> OTHER INFORMATION: Skin-binding peptide

<400> SEQUENCE: 103

His Gln Arg Pro Tyr Leu Thr
1               5

<210> SEQ ID NO 104
<211> LENGTH: 7
<212> TYPE: PRT
<213> ORGANISM: Artificial Sequence
<220> FEATURE:
<223> OTHER INFORMATION: Skin-binding peptide

<400> SEQUENCE: 104

Phe Pro Pro Leu Leu Arg Leu
1               5
```